(12) United States Patent
Wach

(10) Patent No.: US 9,086,533 B1
(45) Date of Patent: Jul. 21, 2015

(54) METHOD AND SYSTEM FOR COUPLING LIGHT THROUGH CHALLENGING MEDIA

(75) Inventor: Michael L. Wach, Alpharetta, GA (US)

(73) Assignee: CIRREX SYSTEMS, LLC, Wilmington, DE (US)

( * ) Notice: Subject to any disclaimer, the term of this patent is extended or adjusted under 35 U.S.C. 154(b) by 496 days.

(21) Appl. No.: 13/134,304

(22) Filed: Jun. 4, 2011

Related U.S. Application Data

(60) Provisional application No. 61/397,096, filed on Jun. 8, 2010.

(51) Int. Cl.
| | |
|---|---|
| *A61B 6/00* | (2006.01) |
| *A61B 8/00* | (2006.01) |
| *G02B 6/42* | (2006.01) |
| *G02B 6/122* | (2006.01) |
| *A61B 18/20* | (2006.01) |
| *G02B 6/032* | (2006.01) |
| *A61B 18/22* | (2006.01) |

(Continued)

(52) U.S. Cl.
CPC ............... *G02B 6/122* (2013.01); *A61B 5/0066* (2013.01); *A61B 5/0075* (2013.01); *A61B 5/0084* (2013.01); *A61B 5/0086* (2013.01); *A61B 5/6853* (2013.01); *A61B 18/24* (2013.01); *A61B 2018/206* (2013.01); *A61B 2018/2222* (2013.01); *A61M 25/10* (2013.01); *G02B 2006/0325* (2013.01)

(58) Field of Classification Search
CPC .............. A61B 18/24; A61B 18/201; A61B 2018/2255; A61B 1/00119; A61B 2018/2222; A61B 2018/206; A61B 5/6853; A61B 5/0075; A61B 5/0066; A61B 5/0084; A61B 5/0086; G02B 6/122; G02B 2006/0325; A61M 25/10

USPC ............................ 600/462, 473, 476; 385/31
See application file for complete search history.

(56) References Cited

U.S. PATENT DOCUMENTS 5,192,278 A * 3/1993 Hayes et al. .................... 606/15
5,570,447 A * 10/1996 Liu ............................... 385/125
(Continued)

FOREIGN PATENT DOCUMENTS

WO    WO 2009/121055    10/2009

OTHER PUBLICATIONS de Matos et al., "Liquid-core, liquid-cladding photonic crystal fibers," Sep. 3, 2007, *Optics Express*, 15(8):11207-11212, 6 pp.
(Continued)

*Primary Examiner* — Long V Le
*Assistant Examiner* — Helene Bor
(74) *Attorney, Agent, or Firm* — Ascenda Law Group, PC

(57) ABSTRACT

An optical path can be created through optically challenging media. Light can transmit over the optical path between an end of an optical waveguide and a point displaced from the end. A fluid that scatters or absorbs light, generates interference, or otherwise poses optical challenges can be disposed between the waveguide end and the point. The optically challenging fluid can comprise blood, turbid and/or opaque fluid, absorbing liquids, or other liquid or fluid presenting transmission issues, for example. An optical path can be formed between the end and the point to facilitate transmitting light through the optically challenging fluid. In certain examples, the optical path can comprise a waveguide formed of fluids emitted into the optically challenging fluid, a gas injected into the optically challenging fluid, or an expandable structure, such as a balloon filled with substantially transparent liquid or gas.

4 Claims, 12 Drawing Sheets

(51) Int. Cl.
*A61B 18/24* (2006.01)
*A61B 5/00* (2006.01)
*A61M 25/10* (2013.01)

(56) References Cited

U.S. PATENT DOCUMENTS

| | | | | |
|---|---|---|---|---|
| 5,573,531 | A * | 11/1996 | Gregory | 606/14 |
| 5,709,653 | A * | 1/1998 | Leone | 604/20 |
| 6,343,174 | B1 * | 1/2002 | Neuberger | 385/123 |
| 6,366,726 | B1 | 4/2002 | Wach et al. | |
| 6,983,093 | B2 * | 1/2006 | Fraval et al. | 385/125 |
| 7,447,408 | B2 * | 11/2008 | Bouma et al. | 385/123 |
| 8,086,083 | B2 * | 12/2011 | Mueller et al. | 385/125 |
| 2007/0010727 | A1 * | 1/2007 | Van Beek et al. | 600/341 |
| 2008/0166089 | A1 * | 7/2008 | Klunder et al. | 385/31 |
| 2009/0112198 | A1 * | 4/2009 | Khanna et al. | 606/15 |

OTHER PUBLICATIONS

Han et al., "Liquid-core Photonic crystal fiber platform for raman scattering measurements of microliter analyte solutions," 2007, Proceedings of SPIE, Abstract only.

Irizar, Juan, "Raman Spectroscopy of Colloidal Nanoparticles in liquid core photonic crystal fibers," 2008, Thesis, Dept of Electrical and Computer Engineering, University of Toronto, 108 pp.

Macomber et al., "Light Guiding Fused Silica Capillary Tubing," Jun. 202, LCGC, The Application Notebook, downloaded from http://www.chromatographyonline.com/lcgc/data/articlestandard/lcgc/372002/31221/articie.pdf, 1 pg.

Spittel et al., "Optical properties of liquid filled photonic crystal fibers," 2009, DGaO Proceedings, http://www.dgao-proceedings.de/download/110/110_c11.pdf, 2 pp.

Yu, Chin-ping et al, "Dual-core liquid-filled photonic crystal fibers for dispersion compensation," Aug. 2008, Proceedings of the 29$^{th}$ URSI General Assembly, downloaded from http://ursi-test.intec.urgent.be/files/URSIGA08/papers/D02bp1.pdf, 4 pp.

Zhang et al., "Liquid core photonic crystal fiber sensor based on surface enhanced Raman scattering," May 2007, Applied Physics Letters, 90(19):193504-13504-3, Abstract only.

Zuowei et al., "Optical Fiber Raman Spectra of $CCl_4$," 1993, Chinese Phys. Letter., 10(7):409-412.

"High Purity Synthetic Fused Silica for Photonic Crystal Fibers," Dec. 2008, v.2.0_E/5TC, downloaded from http://heraeus-quarzglas.com/media/webmedia_local/downloads/broschren_sf/2009_sf/PCF.pdf, 2 pp.

"Highly Fluorine Doped Tubes," Dec. 2008, v. 2.0_E/5TC, downloaded from http://heraeus-quarzglas.com/media/webmedia_local/downloads/broschren_sf/2009_sf/Fluosil_tubes.pdf, 2 pp.

* cited by examiner

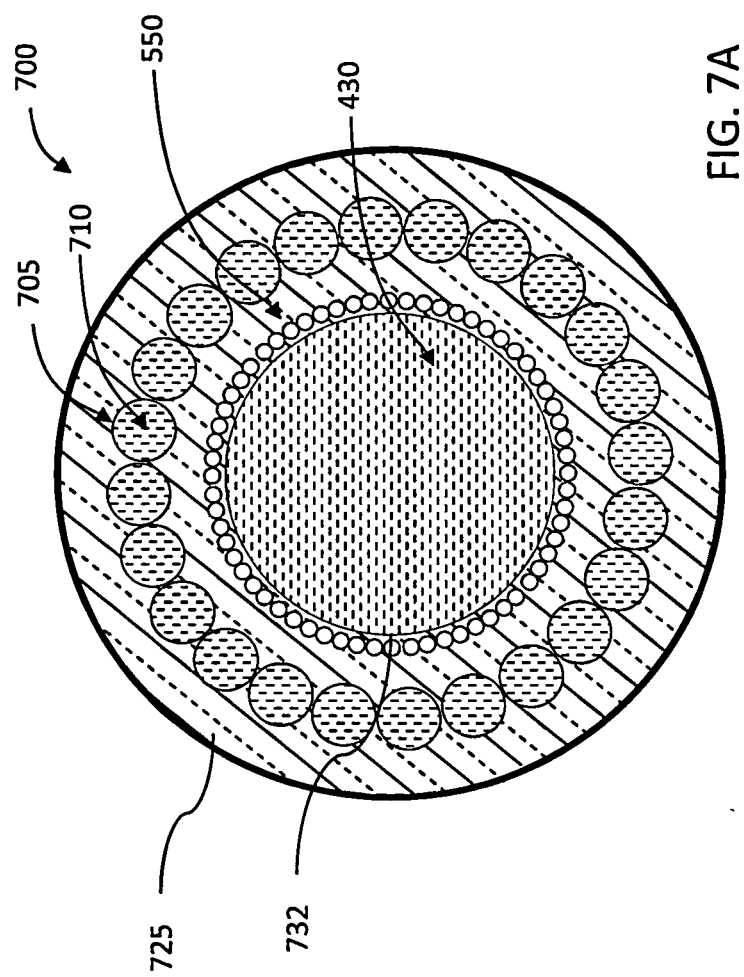

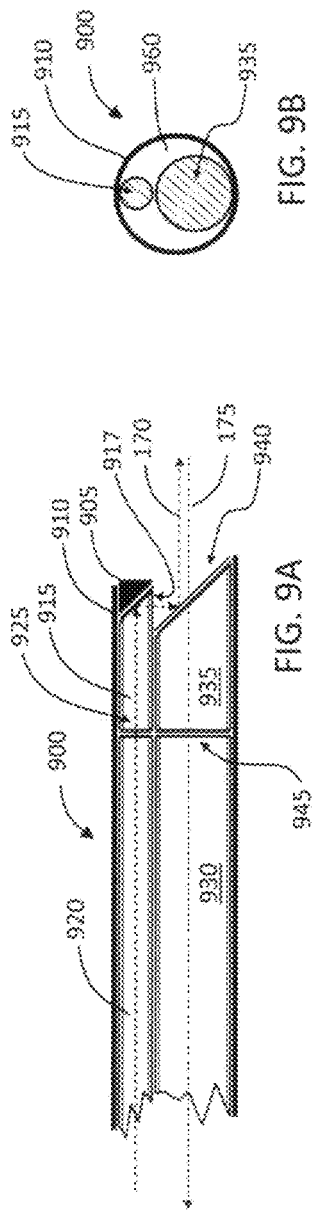
FIG. 9A
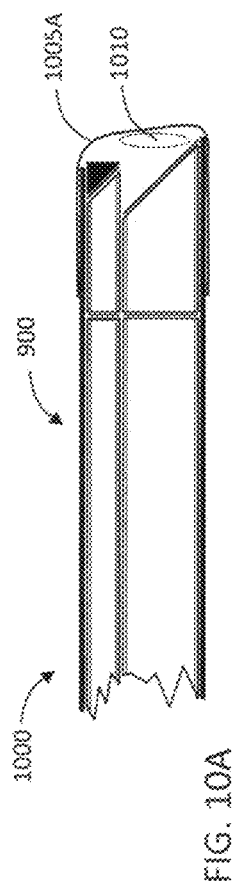
FIG. 9B
FIG. 10A
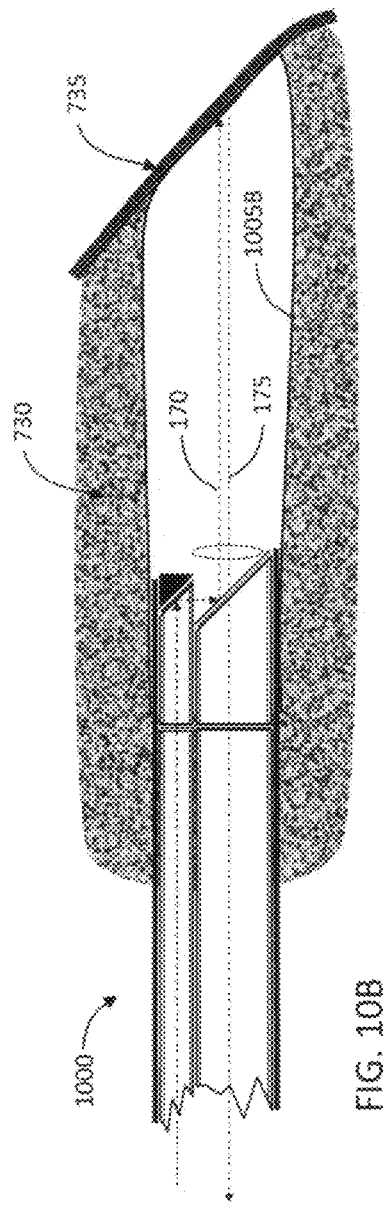
FIG. 10B

METHOD AND SYSTEM FOR COUPLING LIGHT THROUGH CHALLENGING MEDIA

CROSS REFERENCE TO RELATED APPLICATIONS

This application claims priority to U.S. Provisional Patent Application No. 61/397,096, filed Jun. 8, 2010 in the name of Wach and entitled "Method and System for Coupling Light Through Chalenging Media," the entire contents of which are hereby incorporated herein by reference.

TECHNICAL FIELD

The present technology relates generally to characterizing material with light and more specifically to creating an optical path through scattering and/or absorbing media, for example from one or more optical fibers to a material to be analyzed, and transmitting light over the optical path. Among other things, the path can be utilized to evaluate physiologic or biochemical characteristics of in vivo tissue using Raman spectroscopy.

BACKGROUND

Analyzing a sample remotely can entail transmitting light to and from the sample over one or more optical fibers. However, the transmitting light may interact with the optical fibers to impair or complicate the analysis. A number of approaches have been proposed to address competition between light-matter interactions occurring within the optical fibers and light-matter interactions occurring within the sample.

One approach entails transmitting source light from a light source to the sample over a dedicated light-delivery optical fiber and transmitting sample light (stemming from light-matter interactions occurring at the sample) from the sample to a detector over a different, dedicated light-collection optical fiber. An optical system located at the distal end of the optical fibers transfers light to and from the sample. The distal optical system attenuates light due to light-matter interactions occurring within the light-delivery fiber to reduce corruption of the source light associated with transmission from the light source to the sample. The distal optical system may further block the source light from transmitting on the light-collection optical fiber. Excluding the source light from transmitting on the light-collection optical fiber can avoid the source light from causing light-matter interactions in the light-collection optical fiber that would mix with and potentially be difficult to differentiate from the sample light.

While providing segregated light-delivery and light-return paths may offer advantage to some applications, other applications would benefit from delivering and collecting light over one, common optical fiber. However, with conventional technology, the material analysis may struggle to differentiate between light-matter interactions occurring in the bidirectional optical fiber and light-matter interactions occurring in the sample. That is, the source light traveling towards the sample can interact with material of the bidirectional optical fiber and produce light traveling away from the sample that mixes with the sample light that is also traveling away from the sample. For example, in the case of Raman analysis, laser light traveling towards the sample can interact with silica of a conventional bidirectional optical fiber to produce "silica Raman" light and/or fluorescence that may be more intense than the Raman scattered light from the sample (the "Raman light") that is the basis of the material analysis.

Most of the conventional proposals for conducting Raman analysis using a single optical fiber for light delivery and light collection have limitations. One conventional proposal entails conducting Raman analysis outside the fingerprint spectral region of the Raman spectrum, where silica Raman is weak relative to Raman scattering of the sample. However, Raman scattering generally is also weak outside the fingerprint region, resulting in noise. Further, outside the fingerprint region, distinguishing features between or among competing spectra of a sample typically diminish. Accordingly, conducting Raman analyses outside the Raman fingerprint region can be challenging, particularly when the sample has numerous chemical constituents that the analysis seeks to distinguish. The Raman fingerprint region is typically considered to be about 500 $cm^{-1}$ to about 2000 $cm^{-1}$ (wavenumbers) for organic molecules.

Another conventional approach involves a crystal optical fiber transmitting laser light from a laser to a sample and transmitting Raman light from the sample to a detector. Periodically spaced structures in the optical fiber direct the laser light and the Raman light via constructive and destructive interference. One drawback to most conventional approaches for using a crystal optical fiber for transmitting source light and sample light bidirectionally concerns the crystal optical fiber imposing its own spectral signature on the sample light. In other words, conventional crystal optical fibers can have transmission characteristics that deviate across the Raman fingerprint region. For example, spikes, peaks, valleys or undulations in a crystal optical fiber's transmission profile can distort or otherwise impact a Raman spectrum of the sample. Another drawback concerns silica Raman generated as the laser light interacts with the periodically spaced structures and/or propagates between periodically spaced structures. Accordingly, materials and optical characteristics of conventional crystal optical fibers can impose problematic background, artifacts, and/or interference on a spectrum.

Another issue facing many conventional technologies concerns coupling light between the distal end of one or more optical fibers and a sample when the media between that distal end and the sample scatters light, absorbs light, or has challenging light transmission characteristics. In this situation, such challenging media may produce a signal that interferes with the signal of interest from the sample. As another potential problem, the challenging media may diffuse or attenuate the light traveling towards or away from the sample. The challenging media may smear spatial resolution, distort acquired images, or otherwise disturb, confuse, complicate, or confound an analysis.

In view of the foregoing discussion of representative deficiencies in the art, a need exists for improved technologies for analyzing materials over optical fibers and for improved optical fibers and optical waveguides and associated coupling optics. Need is apparent for a system that can transmit source light from a source towards a sample and transmit sample light from the sample towards a detector while avoiding or mitigating interference from lightmatter interactions occurring during transmission. Further need exists for improved technologies for analyzing materials remotely via Raman analysis, including in vivo, in situ, in vitro, and/or ex vivo Raman spectroscopy. Additional need exists for improved technologies for conducting optical coherence tomography ("OCT"), surface enhanced Raman spectroscopy ("SERS"), near infrared ("NIR") analysis, ultraviolet ("UV") or visible ("VIS") spectroscopy, UV resonant Raman spectroscopy ("UVRRS"), imaging, surface plasmon resonance ("SPR"), coherent anti-Stokes Raman scattering ("CARS"), anti-Stokes Raman, Fourier transform Raman ("FT-Raman"), elastic scattering, laser Doppler shift, hyperspectral imaging, surface enhanced resonance Raman spectroscopy ("SERRS"), stimulated Raman, spontaneous Raman, spatially offset Raman spectroscopy ("SORS"), hyper Raman, or some other appropriate analytical technique or instrumentation that utilizes light. Need further exists for light-based characterization of cardiovascular or cardiac tissue over a catheter. Need also exists for an improved system for coupling light into or out of one or more optical fibers. Need exists for technology that can transmit light through optically challenging media, including in, across, or through blood and other biological materials. Need exists for a technology that can form an optical path through media having poor light transmission characteristics. A technology addressing one or more such needs, or some other related shortcoming in the art, would benefit photonics, including promoting in vivo analyses and facilitating new applications.

SUMMARY

The present invention can support creating optical paths through optically challenging media and/or transmitting light between one or more optical fibers and a point displaced from the fibers. In one aspect of the present invention, light can transmit between an end of an optical waveguide and a location that is displaced from the end. A fluid that scatters light, absorbs lights, generates interference, or otherwise presents light transmission challenges can be disposed between the end and the location. The optically challenging fluid can comprise blood, turbid fluid, opaque fluid, absorbing liquids, or other liquid or fluid posing transmission issues, for example. An optical path can be formed between the end and the location to facilitate transmitting light through the optically challenging fluid. In certain examples, the optical path can comprise a waveguide formed of fluids emitted into the optically challenging fluid. In certain examples, the optical path can comprise a gas injected into the optically challenging fluid. In certain examples, the optical path can comprise an expandable structure, such as a balloon filled with substantially transparent liquid or gas. Light can couple between the end of the optical waveguide and the location over the optical path, either towards the optical waveguide, away from the optical waveguide, or bidirectionally, for example. The coupled light can support material analyses, sensing, spectroscopy, illumination, material processing, data transmission, or optical communication, for example.

The discussion of transmitting light presented in this summary is for illustrative purposes only. Various aspects of the present invention may be more clearly understood and appreciated from a review of the following detailed description of the disclosed embodiments and by reference to the figures and claims. Other aspects, systems, processes, methods, features, advantages, benefits, and objects of the present invention will become apparent to one of ordinary skill in the art upon examination of the following detailed description and the accompanying figures. It is intended that all such aspects, systems, processes, methods, features, advantages, benefits, and objects are to be included within this description, are to be within the scope of the present invention, and are to be protected by the accompanying claims.

BRIEF DESCRIPTION OF THE FIGURES

FIGS. 7A and 7B, collectively FIG. 7, are cross sectional views of a system for creating an optical channel through optical challenging media in accordance with certain exemplary embodiments of the present invention.

FIGS. 9A and 9B, collectively FIG. 9, are illustrations of a system for analyzing a material via delivering and collecting light in accordance with certain exemplary embodiments of the present invention.

FIGS. 10A and 10B, collectively FIG. 10, are illustrations of a system for analyzing a material via delivering and collecting light in accordance with certain exemplary embodiments of the present invention.

Figure 1:
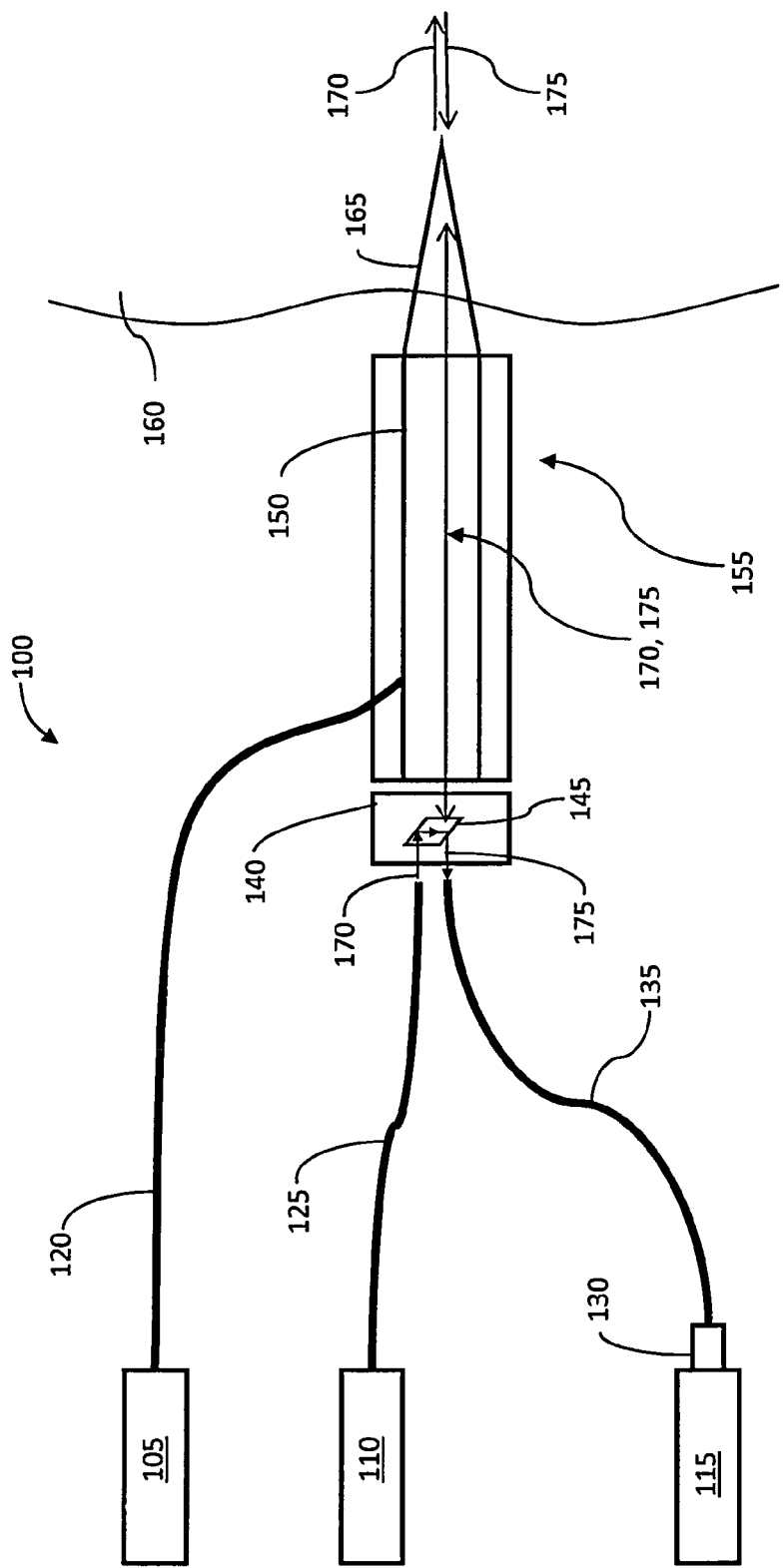
FIG. 1 is a functional block diagram of an instrumentation system that conducting Raman spectroscopy employing a liquid core waveguide in accordance with certain exemplary embodiments of the present invention.

Many aspects of the present invention can be better understood with reference to the above figures. The elements and features shown in the figures are not necessarily to scale, emphasis instead being placed upon clearly illustrating principles of exemplary embodiments of the present invention. Moreover, certain dimensions may be exaggerated to help visually convey such principles. In the figures, reference numerals designate like or corresponding, but not necessarily identical, elements throughout the several views.

DETAILED DESCRIPTION OF EXEMPLARY EMBODIMENTS

The present invention can support forming an optical path through optically challenging media.

Certain exemplary embodiments of the present invention support transmitting light between two locations using an optical waveguide and/or an optical fiber for at least part of the transmission. The transmission can avoid introduction or accumulation of interference on the light and/or disruption, excessive or deleterious scattering, problematic attenuation, or other unwanted effect on the light. Avoiding interference on transmitted light can benefit analytical instrumentation and light-based characterization of materials, such as OCT, SERS, NIR analysis, UV or VIS spectroscopy, UVRRS, imaging, SPR, CARS, anti-Stokes Raman, FT-Raman, elastic scattering, laser Doppler shift, hyperspectral imaging, SERRS, stimulated Raman, spontaneous Raman, SORS, hyper Raman, and various other analyses involving light, to mention a few representative examples.

Certain exemplary embodiments of the present invention support remote Raman spectroscopy utilizing a liquid core waveguide. The liquid core waveguide can transmit light both towards and away from an analyte while maintaining light purity and fidelity and/or avoiding interference, noise, unwanted background, detrimental artifacts, and/or extraneous responses. Fluid disposed in the waveguide can have reduced Raman cross section relative to an adjacent cladding. Bidirectional transmission over the liquid core waveguide can facilitate faster and more efficacious spectroscopy of various medical disorders and biological conditions manifesting altered tissue composition, for example.

Certain exemplary embodiments of the present invention can facilitate analysis within a vasculature of a patient while avoiding clamping the vasculature or otherwise occluding, disrupting, or substantially interfering with blood flow. Thus, light can characterize an analyte inside a vascular lumen while blood flow remains uninterrupted. A catheter can emit a stream of saline solution or other fluid having desirable optical characteristics, with the stream extending through blood within the vasculature. The stream projecting into the blood can comprise a column or jet or plume of fluid, have a substantially cylindrical or elongated form, and/or exhibit symmetry about a longitudinal axis thereof. Light can transmit over this stream between a distal end of the catheter and a sidewall of a vascular lumen. A pump or other appropriate fluid supply system coupled to the catheter can pressurize the fluid to create the stream. In certain exemplary embodiments, the fluid has a higher refractive index than the surrounding medium (e.g. blood or other body fluid), and the stream functions as a waveguide, guiding light to and from an analyte or other investigative site. In certain exemplary embodiments, the stream comprises two components wherein an interface between the two components extends lengthwise and forms a waveguide, reflects light, deflects light, steers light, or bends light.

Accordingly, a catheter or probe can be positioned a standoff distance from an investigative site. An optical challenging material (for example turbid, absorbing, opaque, scattering, etc.) can be disposed in the standoff. The emitted fluid can provide a fluidic waveguide extending across the standoff, from the probe or catheter to the investigative site. The fluidic waveguide can comprise an internally reflective interface, such as between the emitted fluid and an ambient material or between two emitted fluids, for guiding light.

The present invention will be discussed more fully hereinafter with reference to FIGS. 1-11, which provide additional information about representative or illustrative embodiments of the present invention. FIG. 1 describes an exemplary embodiment of an instrumentation system that comprises a liquid core waveguide supporting in vivo Raman spectroscopy. FIGS. 2, 3, 4 5A, and 5B describe exemplary elements and features of the system, including the liquid core waveguide. FIG. 6 describes a process for utilizing a liquid core waveguide and for conducting in vivo Raman spectroscopy. FIGS. 7, 8, 9, and 10 describes systems and methods for creating optical paths through optically challenging media, for example via emitting a two-component fluid stream, emitting gas, or extending a balloon.

The present invention can be embodied in many different forms and should not be construed as limited to the embodiments set forth herein; rather, these embodiments are provided so that this disclosure will be thorough and complete, and will fully convey the scope of the invention to those having ordinary skill in the art. Furthermore, all "examples," "embodiments," and "exemplary embodiments" given herein are intended to be non-limiting, and among others supported by representations of the present invention.

This document includes sentences, paragraphs, and passages (some of which might be viewed as lists) disclosing alternative components, elements, features, functionalities, usages, operations, steps, etc. for various embodiments of the present invention: Unless clearly stated otherwise, all such lists, sentences, paragraphs, passages, and other disclosures are not exhaustive, are not limiting, are provided in the context of describing representative examples and variations, and are among others supported by various embodiments of the present invention. Moreover, the items in such lists and other disclosed alternatives are not necessarily mutually exclusive and thus may be overlapping. A single embodiment of the present invention or a single element can include multiple items from a disclosed set of alternatives, whether the set is disclosed herein using the conjunction "or," in the form of a Markush group, as a list, or otherwise enumerated. Those of ordinary skill in the art having benefit of this disclosure will appreciate that the present invention is not constrained by any such lists, examples, or alternatives. Moreover, the inclusion of lists, examples, embodiments, and the like will help educate and guide those of ordinary skill in the art to practice many more implementations and instances of the present invention without undue experimentation, all of which are intended to be within the scope of the claims.

This disclosure includes figures and discussion in which features and elements of certain embodiments may be organized into functional blocks, subsystems, modules, or the like. Further, certain processes and methods may be organized into steps. Such organization is intended to enhance readership and to teach the reader about working principles of the present invention and about making and using an abundance of embodiments of the present invention. The organization is not intended to force any rigid divisions or partitions that would limit the present invention. In practice, the flexibility of the present invention supports dispersing, rearranging, or grouping functionalities, elements, and features in many different ways. The inclusion of an element or function in one block, module, or subsystem verses another can be substantially arbitrary in many instances, with the divisions being soft and readily redrawn using this rich disclosure supported by ordinary skill. Accordingly, functional blocks, modules, subsystems, and the like can be combined, divided, repartitioned, redrawn, moved, reorganized, rearranged, or otherwise altered without deviating from the scope and spirit of the present invention. This is not to say that certain disclosed organizations and combinations are not novel or are obvious. The way certain features of the present invention relate to and interact with one another is new. Accordingly, combinations, arrangements, or organizations disclosed herein can represent innovative subject matter.

Turning now to FIG. 1, this figure illustrates a functional block diagram of an exemplary instrumentation system 100 that conducts Raman spectroscopy according to certain embodiments of the present invention. The instrumentation system 100 assays tissue 160 via analyzing the tissue's photonic response to illumination.

The instrumentation system 100 comprises a laser 110 outputting excitation light 170 that transmits through an optical fiber 125 and into a catheter 155. In an exemplary embodiment, the laser 110 comprises a semiconductor laser outputting monochromatic laser light having a wavelength between about 750 nanometers ("nm") and about 900 nm, such as about 830 nm. Various other embodiments can provide different wavelengths of monochromatic, multicolored, polychromatic, laser, ultraviolet, visible, near infrared ("NIR"), incandescent, light emitting diode ("LED"), or white light, for example.

As discussed in further detail below, in certain embodiments, the exemplary catheter 155 comprises a waveguide 150 that comprises a liquid core, for example comprising saline or an aqueous solution that comprises a dissolved substance. As will be discussed in further detail below with respect to FIGS. 7 and 8, in certain exemplary embodiments, the exemplary catheter 155 can emit a two-component stream of fluid forming a column of fluids that guides light. The liquid core waveguide 150 optically couples to the optical fiber 125 via a filter system 140. In an exemplary embodiment, the optical fiber 125 impregnates the core of the liquid core waveguide 150 with excitation light 170.

As illustrated in FIG. 1, a pump 105 and an associated reservoir (not illustrated) feeds the liquid to the fluid supply line 120. The fluid supply line 120, in turn, supplies the liquid to the catheter 155. As discussed in further detail below, the supplied liquid fills the core of the liquid core waveguide 150.

A needle 165 is disposed at the distal end of the catheter 155 for penetrating the tissue 160. The tip of the needle 165 comprises an aperture (see FIG. 3) through which the excitation light 170 transmits to the tissue 160 and the return light 175 transmits back. In certain exemplary embodiments, the liquid impregnated with excitation light 170 passes to the tissue 160 through the aperture. In certain exemplary embodiments, the liquid has multiple components for waveguiding light after the light has emitted from the needle 165. Responsive to illumination by the excitation light 170, the tissue 160 produces or otherwise emits the return light 175, which passes back through the aperture and is coupled to the liquid core waveguide 150.

Although FIG. 1 illustrates an exemplary embodiment in which the liquid, the excitation light 170, and the return light 175 can pass through a common aperture, other embodiments, may have multiple apertures. For example, the liquid may exit the catheter 150 through a dedicated aperture. Further, in certain exemplary embodiments, the liquid may be sealed within the catheter 150 rather than flowing. That is, the liquid core waveguide 150 can be sealed or otherwise encapsulate the liquid. In certain exemplary embodiments, the excitation light 170 passes through one dedicated aperture, and the return light 165 passes through another dedicated aperture.

Referring to FIG. 1, the liquid core waveguide 150 transmits the return light 175 to the optical fiber 135 via the filter system 140. The optical fiber 135 transmits the return light 175 to the adapter 130 which couples the optical fiber 135 to the detector 115. In certain exemplary embodiments, the adapter 130 changes the geometric format of the output of the optical fiber 135, for example converting a circular light pattern into a linear light pattern.

In an exemplary embodiment, the detector 115 comprises a spectrometer system that spectrally analyzes the return light 175, for example comprising a spectrograph or spectrometer coupled to a charge coupled device ("CCD"). In an exemplary embodiment, the spectrometer system can comprise a computer system that determines a state, condition, or parameter of the tissue 160 according to spectral characteristics of the return light 175. For example, the detector 115 can identify a tumor boundary or distinguish vulnerable plaque in a vasculature from relatively benign plaque according to Raman spectra of the tissue 160.

The filter system 140 comprises a dichroic mirror system 145 that distinguishes and/or separates the excitation light 170 traveling towards the tissue 160 from the return light 175 traveling away from the tissue 160, opposite the excitation light 170. As will be discussed in further detail below, the filter system 140 couples the outgoing excitation light 170 from the optical fiber 125 into the liquid core waveguide 150 and couples the incoming return light 175 from the liquid core waveguide 150 into the optical fiber 135.

The term "waveguide" or "optical waveguide," as used herein, generally refers to a system, device, or structure that directs, controls, or steers light to flow along a path, course, route, or channel and confines, limits, or binds the light so that the light generally stays on or in the path, course, route, or channel. An optical waveguide can comprise one or more structures or materials that guide and/or generally confine light during transmission. For example, an optical waveguide can comprise an elongate or elongated section of optical material, such as a core, that has a high refractive index relative to the refractive index of circumferentially adjacent material, such as a cladding. In certain examples, the cladding can comprise a generally cylindrical, hollow, flexible tube with the core comprising a high-index fluid filling the tube. In certain examples, an optical waveguide can further be a stream of liquid having a relatively high refractive index that is circumferentially surrounded by a liquid having a lower refractive index, such that an interface between the two liquids supports internal reflection.

Figure 2:
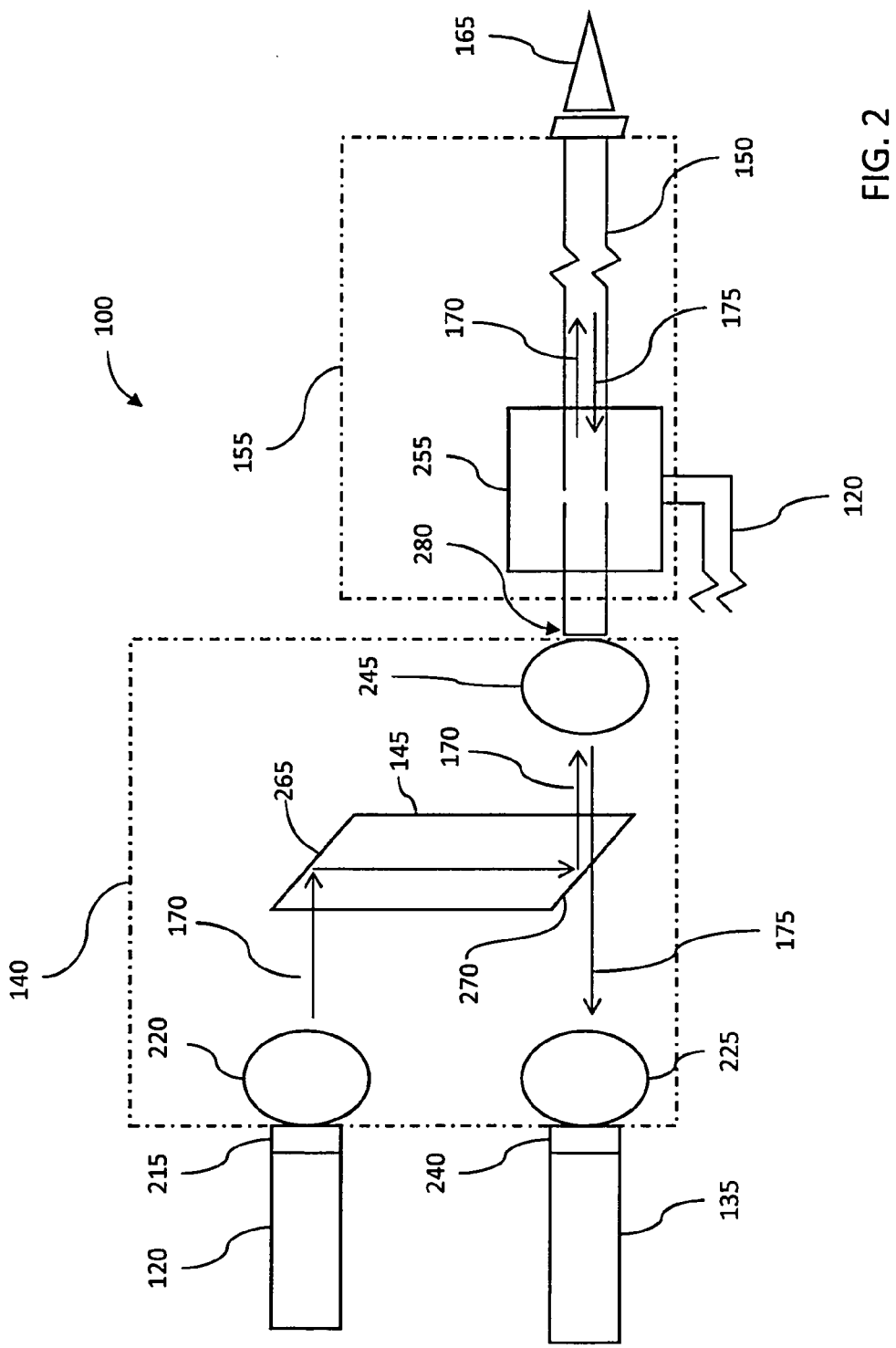
FIG. 2 is a functional block diagram providing an expanded view of an instrumentation system that conducts Raman spectroscopy employing a liquid core waveguide in accordance with certain exemplary embodiments of the present invention.

Turning now to FIG. 2, this figure illustrates a functional block diagram providing an exemplary expanded view of the instrumentation system 100 illustrated in FIG. 1 and discussed above. In particular, FIG. 2 describes additional details about the catheter 155 and the filter system 140 as well as certain other elements.

In operation of the instrumentation system 100, the excitation light 170 transmits along the optical fiber 120 and through a filter 215 to a ball lens 220. In an exemplary embodiment, the filter 215 comprises a bandpass filter that suppresses any interference, such as silica Raman or fluorescent light, generated by transmission over the optical fiber 205 and may comprise a thin-film interference filter. The ball lens 120 substantially collimates the excitation light 170 and/or projects the excitation light 170 onto a mirrored surface 265 of the dichroic mirror system 145. The mirrored surface 265 can comprise a reflective metallic coating, such as a gold coating, or a dielectric mirror or filter. In an exemplary embodiment, the dichroic mirror system 145 comprises a prism or a single block of silica to which the mirror surface 265 and a filtered surface 270 adheres.

The mirrored surface 265 reflects the excitation light 170 to the filtered surface 270 of the dichroic mirror system 145. The filtered surface 270 reflects the excitation light 170 towards another ball lens 245, which focuses the excitation light 170 into the proximal end 280 of the liquid core waveguide 150. In an exemplary embodiment, the filtered surface 270 comprises a bandstop filter, which can be implemented as a thin-film interference filter. The liquid core waveguide 150 transmits the excitation light 170 to the needle 165, which emits the excitation light 170 to the tissue 160, as discussed above. In certain exemplary embodiments, the needle 165 can be replaced with a catheter tip that is flexible and/or conducive to positioning lengthwise in a vascular lumen and guiding through such a lumen.

The liquid core waveguide 150 transmits the return light 175 from the needle 165 towards the filter system 140 while transmitting the excitation light 170 towards the needle 165. The return light 175 emits from the liquid core waveguide 150 onto the ball lens 245, which collimates the return light 175 while simultaneously focusing the excitation light 170 in the opposite direction as discussed above. The filter 270 transmits the return light 175 to a ball lens 225 that directs and/or focuses the return light 175 through the filter 240 and into the optical fiber 135, for propagation to the detector 115. The filter 240 can comprise a reject filter for blocking residual amounts of the excitation light 170 transmitting through the filter 270.

Although FIG. 2 illustrates the filter system 140 disposed outside the catheter 155, in certain exemplary embodiments, the filter system 140 can be located within the catheter 155. Accordingly, in certain exemplary embodiments, the optical fibers 120 and 135 extend into the catheter 155. For example, the liquid core waveguide 150 might have a length in a range of about 5 to 50 centimeters within a catheter having a length of about one meter.

As will be discussed in further detail below with respect to FIG. 4, the fluid fitting 255 couples fluid from the fluid supply line 120 into the liquid core waveguide 150. In certain exemplary embodiments, the fluid supply line 120 charges the liquid core waveguide 150 with saline.

While FIG. 2 illustrates the fluid fitting 255 disposed within the catheter 155, in certain exemplary embodiments, the fluid fitting 255 can be external. For example, in certain exemplary embodiments, the liquid core waveguide 150 can have a length that is about 10 to 25 percent longer than the catheter 155, with the fluid fitting 255 attached to a portion of the liquid core waveguide 150 that extends past the catheter 155.

Figure 3:
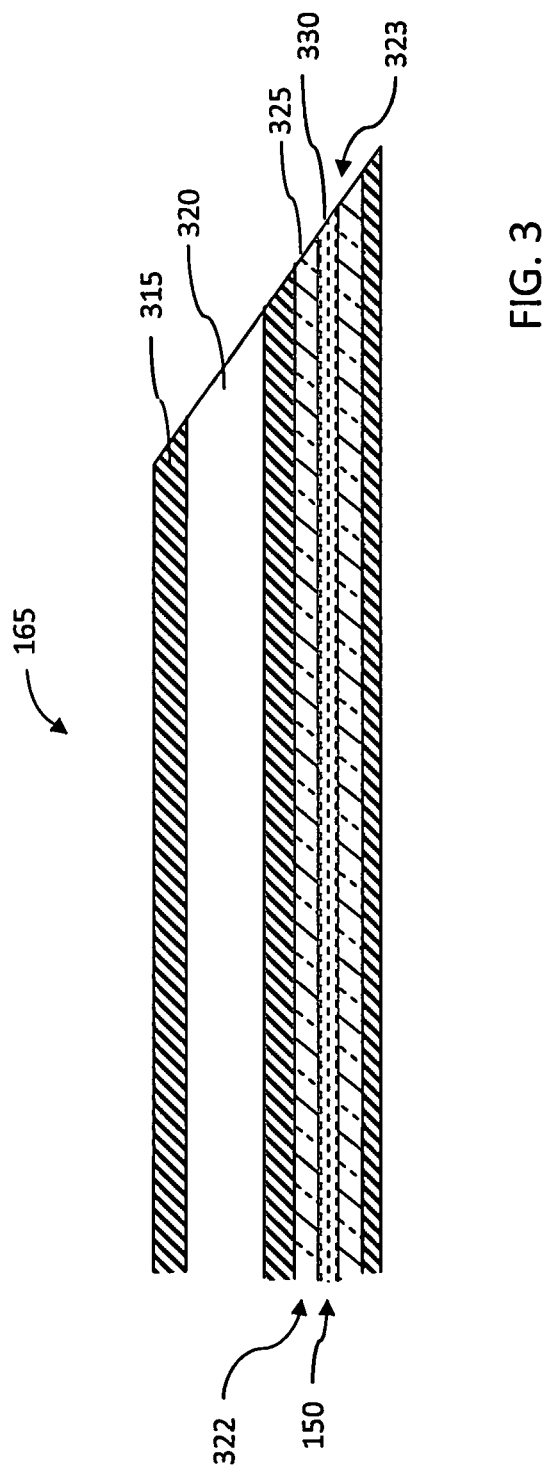
FIG. 3 is an illustration of a distal end of an instrumentation system that conducts Raman spectroscopy employing a liquid core waveguide and comprising a needle through which the liquid core waveguide passes in accordance with certain exemplary embodiments of the present invention.

Turning now to FIG. 3, this figure is an expanded view of an exemplary embodiment of the needle 165. The needle 165 comprises a body 315 comprising a metallic composition, such as stainless steel, or other biocompatible material suitable for puncturing or penetrating tissue 160. Accordingly, the needle 165 can be utilized for in vivo analysis, such as via insertion into a human, mammal, vertebrate, organism, test subject, patient, or living tissue; deployed for in situ analysis of materials or processes; or utilized on ex vivo or in vitro tissues or extracted specimens, for example. As an alternative to a substantially rigid puncturing device, in certain exemplary embodiments, a flexible end such as a steerable catheter tip can be substituted for the needle 165. The needle 165 comprises an inner lumen 320 that can be used to deliver a therapeutic agent, such as a pharmaceutical compound or other material that is operative to provide therapeutic benefit or that is under investigation as a candidate that might provide therapeutic benefit.

In certain exemplary embodiments, the inner lumen 320 can deliver a fluid or liquid (which may be a mixture or a suspension) that facilitates analysis or assay of the tissue 160 or another material, sample, organ, or analyte disposed adjacent the needle 165. In accordance with various exemplary embodiments, the inner lumen 320 can deliver a fluid that comprises a dye; a fluorescent material; one or more tags; an indicator; a sensing compound; a material that, when appropriately illuminated, fluoresces in the presence of a physical condition, disease state, tissue condition, chemical condition, or other parameter or stimulus of interest; a chemical probe; a fluorescent probe; a fluorescent or other probe for detecting or sensing and/or quantitatively analyzing one or more reactive oxygen species, such as superoxide and/or hydroxyl radicals; a reduced dye probe for detection of radical oxygen species; a stain; a reference material; a contrast agent; a signal enhancer; quantum dots; nanoparticles; a material that induces, undergoes, or facilitates SERS or surface enhanced Raman scattering; an agent that induces, facilitates, causes, or stimulates an optical response; a material that undergoes or produces a color or spectroscopic change or optical response in the presence of an analyte of interest; a reactant; a reagent; a fluid that is useful for diagnostics; a diagnostic material; a reaction initiator; a catalyst; or some other useful agent or combination thereof, to mention a few representative examples.

In certain exemplary embodiments, the inner lumen 320 delivers a pharmaceutical agent, drug, or other therapeutic material or agent to the tissue 160 in connection with evaluating interaction between the delivered agent and the tissue 160. For example, the instrumentation system 100 can evaluate drug-tissue interactions for research and development or for clinical applications. In certain exemplary embodiments, the instrumentation system 100 evaluates pharmacokinetics or one or more in vivo effects of a drug or other material introduced into a mammal via the inner lumen 320. In certain exemplary embodiments, the instrumentation system 100 evaluates or identifies a physiological response or change associated with or stemming from delivery of a substance through the inner lumen 320. In certain exemplary embodiments, the instrumentation system 100 quantitatively analyzes pharmacokinetics or one or more in vivo responses of a patient to a drug or other material passing through the inner lumen 320. In certain exemplary embodiments, the instrumentation system 100 assesses dynamic or real-time responses of tissue 160 to therapies, pharmaceutical activity and related physiological changes induced by drug delivery, subtle disease states, tumor boundaries, composition of atherosclerotic plaques, or another biological and/or biochemical parameter relevant to pharmaceutical research and/or clinical procedures. In certain exemplary embodiments, the instrumentation system 100 analyzes changes in a delivered agent, such as a physical or chemical change, resulting from introduction into the tissue 160.

For example, a pharmaceutical manufacturer or developer may want to investigate how a pharmaceutical agent responds to the tissue 160 and/or how the tissue 160 responds to a pharmaceutical agent. The needle 165 can be inserted into the tissue 160 and/or disposed against or near the tissue 160. So oriented, the needle 165 can emit the agent onto or into the tissue 160 through the inner lumen 320. The instrumentation system 100 can then deliver light to and collect light from the tissue 160 and/or the emitted or emitting agent to conduct light-based characterization of the delivered pharmaceutical agent and/or the tissue 160. For example, the needle can emit the excitation light 170 and collect the return light 175 to characterize the tissue 160 and/or the pharmaceutical agent. Accordingly, the instrumentation system 100 can provide information that narrows the field of drug candidates, qualifies drug candidates, refines drugs or drug candidates, and/or substantiates the efficacy of a drug or material introduced into a living organism, which may be human, mammalian, or non-mammalian.

Beyond drug developmental and research and development applications, the needle 165 can be utilized in therapy and/or clinical applications so that effectiveness of a treatment on an individual patient can be assessed, thereby supporting personalized medicine. For example, test quantities of multiple agents can be injected into a tumor (either at the same time or sequentially) through the inner lumen 320 (or through multiple lumens in the needle 165). The instrumentation system 100 can then evaluate the tumor's responses to the individual agents, for example based on oxidation, inflammation, superoxide, reactive oxygen species, hydroxyl radicals, or metabolites. A dose of the agent that generated the greatest beneficial response can then be delivered for therapeutic effect or patient benefit.

In this manner, responses of tumors or lesions to various therapies, treatments, compounds, drugs, toxins, bacteria, viruses, yeasts, pathogens, parasites, cells, stem cells, progenitor cells, cells that can and/or do differentiate, therapeutic cells, therapeutic agents, and/or pharmaceutical agents can be assessed and/or investigated. The technique is further applicable to numerous organs, tissues, and disease states, including cardiovascular disease, atherosclerosis, brain tissue, adipose tissue, pancreases, kidneys, skin, colon, stomach, esophagus, intestines, necrotic myocardial tissue, ischemic myocardial tissue, vasculature, digestive tract, thyroid, spleen, liver, auditory system, ocular organs, eyes, ears, esophagus, blood, bladder, prostate, uterine tissue, reproductive systems, ovaries, circulatory system, lymphatic system, throat, lungs, bone marrow, cartilage, muscular tissue, myocardial tissues, and nerves, and various diseases and treatments thereof, to name a few representative examples.

In certain exemplary embodiments, the inner lumen 320 delivers stem cells to infracted myocardial tissue, an injured spinal cord, or infracted brain tissue of a living laboratory animal in which the needle 165 has been inserted. The instrumentation system 100 can then monitor response of the animal's myocardial tissue, spinal cord, or brain tissue to the stem cells and can further monitor response of the stem cells to delivery in such living tissue. With the needle 165 so disposed, an investigator or medical practitioner can monitor responses and changes over seconds, minutes, hours, days, weeks, or months, for example. The investigator or practitioner gains a real-time window into changes that might otherwise be too subtle or fleeting to detect utilizing convention, post-mortem analysis. In this manner, the investigator can develop effective therapies and protocols and can observe responses that would otherwise be hidden. For example, the instrumentation system 100 can conduct a Raman analysis to determine metabolites and/or metabolic responses at a precise treatment area, such as within a tumor.

In certain exemplary embodiments, the inner lumen 320 delivers a substance that indicates oxidation, presence and/or concentration of a reactive oxygen species, a radical oxygen species, superoxide, and/or hydroxyl radicals occurring in the tissue 160 and/or inflammation, such as one or more of the substances, agents, probes, dyes, or other materials disclosed in the patent application published as International Publication Number WO 2009/121,055 entitled "Reduced Dye Probes for the Detection of Radical Oxygen Species" and naming Niren Murthy, Robert W. Taylor, Kousik Kundu, and Sarah F. Knight as inventors. The entire contents of International Publication Number WO 2009/121,055 entitled "Reduced Dye Probes for the Detection of Radical Oxygen Species" and naming Niren Murthy, Robert W. Taylor, Kousik Kundu, and Sarah F. Knight as inventors are hereby incorporated herein by reference without limitation. For example, the needle 165 can be disposed adjacent tissue of interest, such as the tissue 160, including in a diseased vascular lumen, artery, or blood vessel of a patient or test subject or in or adjacent a tumor of a patient or test subject. With the needle 165 disposed lengthwise in a vascular lumen adjacent an atherosclerotic lesion or plaque, the instrumentation system 100 can evaluate propensity of one or more plaques to rupture based on fluorescence response of the delivered substance to excitation light. (In certain embodiments, a flexible steering element can be substituted for the needle 165.) A plaque having a low vulnerability to rupture, and thus representing a relatively low risk, typically produces relatively low fluorescence as its inflammation and oxidation is low. Conversely, "vulnerable plaque" typically produces heightened fluorescence from the substance.

Accordingly, in certain exemplary embodiments, the instrumentation system 100 comprises one or more channels for delivering a material that facilitates light-based characterization of an adjacent analyte or a sample, which may be either in situ or extracted. As discussed above, such a material can have a fluorescence response that changes according to composition and/or disease state of the analyte or sample. The term "analyte," as used herein, generally refers to a substance or biological or chemical constituent that is the subject of analysis. (In the event that any document incorporated by reference might be interpreted as supporting a different usage for the term "analyte," the usage in the preceding sentence should apply to the claims of the present application as well as the claims of any patent issuing on the present patent application and the claims of any patent(s) claiming priority to the present application.) In certain exemplary embodiments, the delivered material can comprise a reagent. The term "reagent," as used herein, generally refers to a substance having chemical and/or biological activity for detecting, measuring, or otherwise analyzing one or more other substances. (In the event that any document incorporated by reference might be interpreted as supporting a different usage for the term "reagent," the usage in the preceding sentence should apply to the claims of the present application as well as the claims of any patent issuing on the present patent application and the claims of any patent(s) claiming priority to the present application.) The light-based characterization can be a quantitative assay, for example.

In certain exemplary embodiments, the instrumentation system 100 comprises one or more channels for delivering an indicator or a reagent to facilitate in vivo analysis of tissue 160 or other materials disposed in an organism. In certain exemplary embodiments, the instrumentation system 100 comprises multiple channels, each delivering a different reagent, either simultaneously or sequentially. One reagent may be used for a reference, while another reagent may trigger a tissue or drug response or reaction. In certain exemplary embodiments, the two reagents interact with one another when combined at the tip of the needle 165, for example to facilitate an in vivo assay. In certain exemplary embodiments, two materials emitted from the needle 165 undergo a chemical reaction with one another after emission, and the reaction product facilitates an assay or analysis.

In certain exemplary embodiments, a fluid emitted from the inner lumen 320 comprises a fluorescent probe operable to detect presence in the tissue 160 of one or more of a reactive oxygen species, superoxide, inflammation, or a hydroxyl radical. In certain embodiments, the needle 165 places in contact with the tissue 160 a material that comprises a fluorescent probe or chemical that responds to one or more reactive oxygen species and/or to inflammation. In certain embodiments, a material emitted from the inner lumen 320 detects presence and/or determines concentration of reactive oxygen species, superoxide, or hydroxyl radical.

As illustrated in FIG. 3, the liquid core waveguide 150 is disposed in a second lumen 322 of the needle 165. The liquid core waveguide 150 extends to the distal end of the needle 165. The liquid exits, excitation light 170 emits, and return light 175 passes through the aperture 323. In an exemplary embodiment, the core 330 and the circumscribing cladding 325 of the liquid core waveguide 150 defines the aperture. As discussed in further detail below, in certain exemplary embodiments, the liquid core waveguide 150 extends or projects outside the needle 165, for example via emitting multiple liquids of differing refractive indices that collaborate to guide light.

In certain exemplary embodiments, the needle 165 is replaced with a cutting instrument, such that a scalpel or other surgical utensil can conduct a tissue assay during an operation, or with an ablating laser delivery system, for example. Various handheld tools used in surgery and other medical procedures can comprise a channel through which the liquid core waveguide 150 extends to facilitate a remote, real-time assay. Accordingly, measurements obtained during surgery or interventional cardiology procedures or during other medical procedures can provide feedback and/or guidance to a physician, surgeon, or other medical practitioner.

Figure 4:
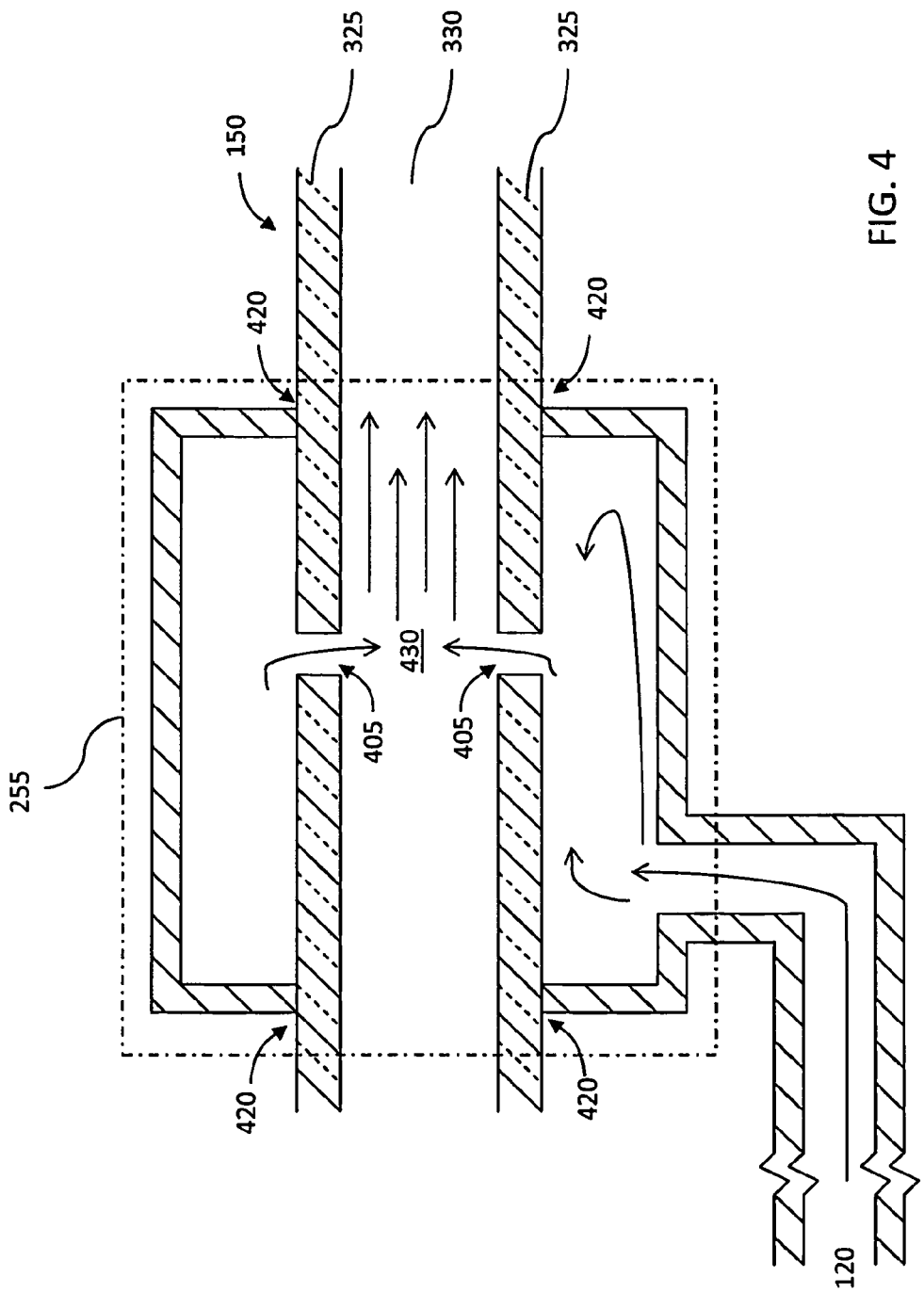
FIG. 4 is an illustration of a fluid system for a liquid core waveguide in accordance with certain exemplary embodiments of the present invention.

Turning now to FIG. 4, this figure is a cross sectional illustration of an exemplary embodiment of the fluid fitting 255. The fluid supply line 120 feeds the fluid 430 to one or more fluid ports 405 where the fluid 430 flows into the liquid core waveguide 150, filling and flowing through the core 330. In an exemplary embodiment, the fluid ports 405 can comprise an array or pattern of holes laser drilled through the cladding 325 of the liquid core waveguide 150. In an exemplary embodiment, the cladding 325 of the liquid core waveguide 150 comprises silica, silicate, or glass capillary tubing. In an exemplary embodiment, the fluid fitting 255 clamps or screw-tightens onto the liquid core waveguide 150 with a gasket or o-ring seal (not illustrated) at the joints 420. In support of internal reflection, the cladding 325 typically has a substantially lower refractive index than the fluid 430 disposed in the core 330.

Figure 5A:
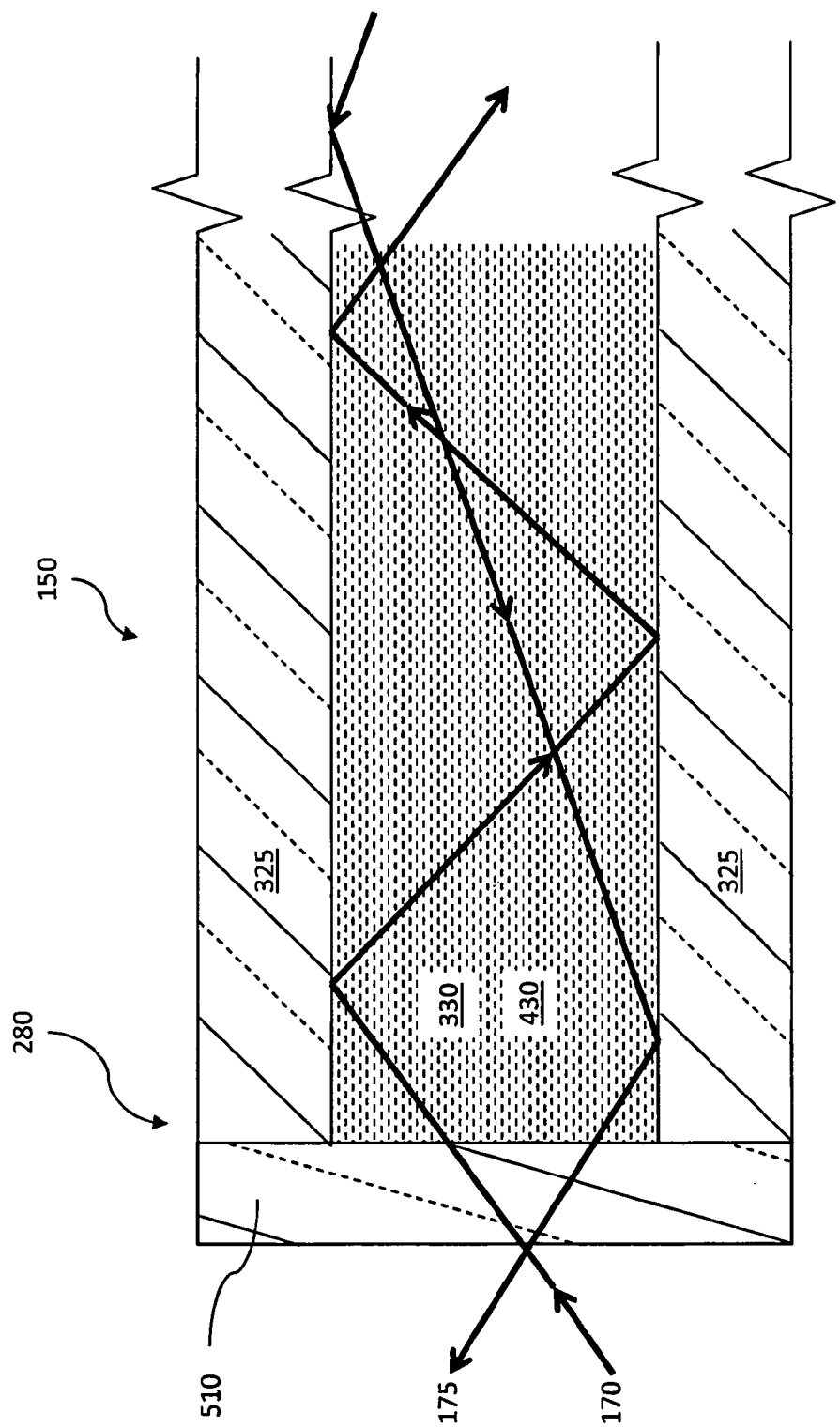
FIG. 5A is an illustration of light carrying capabilities of a liquid core waveguide in accordance with certain exemplary embodiments of the present invention.
Figure 6:
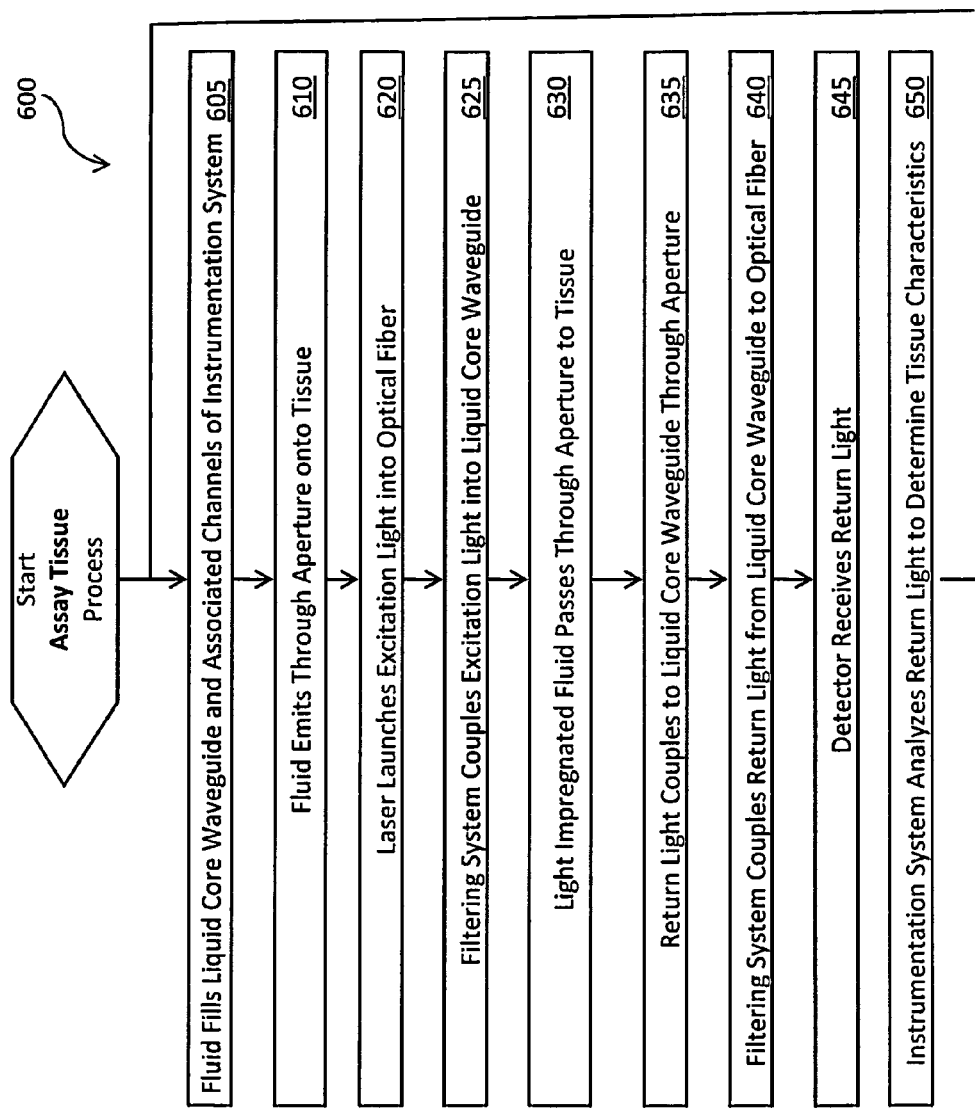
FIG. 6 is a flow chart of a process for analyzing a material utilizing a liquid core waveguide in accordance with certain exemplary embodiments of the present invention.

Turning now to FIG. 5A, this figure is an illustration of an exemplary embodiment of the proximal end 280 of the liquid core waveguide 150. The illustrated proximal end 280 comprises a window 510 keeping the fluid 430 within the liquid core waveguide 150 while facilitating light transmission. Accordingly, in the illustrated embodiment, the fluid 430 flows towards the needle 165. In various exemplary embodiments, the window 510 can comprise silica, sapphire, calcium fluoride, or other substantially transparent material having desirable optical characteristics and/or a desirable or low Raman cross section. The excitation light 170 transmits towards the tissue 160, and the return light 175 transmits away from the tissue 160, both passing through the window 510.

In certain exemplary embodiments, the cladding 325 comprises silica, has a silica-based composition, or substantially consists of silica. In certain exemplary embodiments, the cladding 325 comprises doped silica. In certain exemplary embodiments, the cladding 325 is fused silica. In certain exemplary embodiments, the cladding 325 comprises quartz. In certain exemplary embodiments, the cladding 325 substantially consists of quartz. In certain exemplary embodiments, the cladding 325 substantially consists of silicon dioxide. In certain exemplary embodiments, the cladding 325 can comprise any one or more of the materials disclosed in this paragraph with gaseous inclusions therein, as will be discussed in further detail below with reference to FIG. 5B. In certain exemplary embodiments, the cladding 325 substantially consists of inorganic materials or is inorganic. In certain exemplary embodiments, the cladding 325 is a flexible silica capillary tubing as available from Polymicro Technologies of Phoenix, Ariz. Such tubing can have an outer diameter in a range of 50 to 200 microns and an inner diameter in a range of 10 to 150 microns, for example. In certain exemplary embodiments, such tubing can have an inner diameter in a range of 10 to 50 microns.

In certain exemplary embodiments, the cladding 325 comprises or substantially consists of calcium fluoride or magnesium fluoride. In certain exemplary embodiments, the liquid core waveguide 150 is a flexible tube having a composition of calcium fluoride or magnesium fluoride, with the fluid 430 disposed therein and having a refractive index above that of calcium fluoride or magnesium fluoride. In certain exemplary embodiments, the liquid core waveguide 150 comprises a flexible fused silica capillary tube having an interior coating of calcium fluoride or magnesium fluoride to provide a reduced refractive index at the interface with the fluid 430.

In certain exemplary embodiments, the fluid 430 comprises or is saline. In certain exemplary embodiments, the fluid 430 is normal saline. In certain exemplary embodiments, the fluid 430 is a solution of 0.91 percent weight/volume of sodium chloride (NaCl). In certain exemplary embodiments, the fluid 430 is about 300 mOsm/L. In certain exemplary embodiments, the fluid 430 is physiological saline or isotonic saline. In certain exemplary embodiments, the fluid 430 has a composition of about nine grams of NaCl per liter of water. In certain exemplary embodiments, the fluid 430 has a degree of osmolarity approximating blood or blood plasma or slightly elevated above that of blood or blood plasma. In certain exemplary embodiments, the osmolarity of the fluid 430 approximates or approaches the osmolarity of NaCl in blood or blood plasma. In certain exemplary embodiments, the fluid 430 has a salinity that substantially matches the salinity of blood or blood plasma. In certain exemplary embodiments, the fluid 430 has an electrical conductivity approximating or elevated above that of blood or blood plasma. In certain exemplary embodiments, the fluid 430 has a refractive index that is elevated above the refractive index of blood or blood plasma. In certain exemplary embodiments, the fluid 430 is buffered and/or comprises a buffer. In certain exemplary embodiments, the fluid 430 has a composition that comprises salt, water, and one or more additives or agents having therapeutic, curative, or physiology benefit. In certain exemplary embodiments, the fluid 430 comprises, per liter, about 130 mEq of sodium ion, about 109 mEq of chloride ion, about 28 mEq of lactate, about 4 mEq of potassium ion, and about 3 mEq of calcium ion. In certain exemplary embodiments, the fluid 430 comprises sodium chloride, sodium lactate, calcium chloride, and/or potassium chloride. In certain exemplary embodiments, the fluid 430 is an alkalinizing solution. In certain exemplary embodiments, the fluid 430 is a saline solution. In certain exemplary embodiments, the fluid 430 substantially consists of inorganic ingredients or is substantially inorganic. In certain exemplary embodiments, the fluid 430 substantially consists of biocompatible ingredients or constituents. In certain exemplary embodiments, the fluid 430 has a refractive index above the refractive index of fused silica at the wavelength(s) of the excitation light 170 and/or the return light 175. In certain exemplary embodiments, the fluid 430 is saturated. In certain exemplary embodiments, the fluid 430 is saturated salt. In certain exemplary embodiments, the fluid 430 is saturated with NaCl.

In certain exemplary embodiments, the fluid 430 has a Raman spectrum that is substantially outside the fingerprint region. The fluid 430 can comprise water. In certain exemplary embodiments, the most intense Raman bands or Raman peaks of the fluid 430 are disposed outside the fingerprint region of the Raman spectrum. The fluid 430 can comprise an aqueous solution. In certain exemplary embodiments, the fluid 430 has a Raman spectrum that is substantially displaced from the fingerprint region and/or the spectral region that the instrumentation system 100 uses for assaying the tissue 160.

In an exemplary embodiment, the fluid 430 exhibits lower Raman scattering than the cladding 325 (under substantially common test conditions).

In certain exemplary embodiments, the fluid 430 has a composition that varies deliberately during a medical procedure. In certain exemplary embodiments, a medical practitioner, a researcher, or an automated machine injects or adds a pharmaceutical agent or other substance into the fluid 430, such as at the pump 105. The agent travels with the fluid 430 through the fluid supply line 120 and the liquid core waveguide 150 and is delivered to the tissue 160 through the aperture 323. Once the agent clears the liquid core waveguide 150, the instrumentation system 100 can assay the tissue 160 to assess the effect of the agent on a disease state or other condition of the tissue 160. Further, the instrumentation system 100 can compare spectra taken prior to agent delivery to spectra taken after agent delivery. In this manner, the instrumentation system 100 can track and evaluate drug-tissue interactions and healing over multiple drug administrations. Moreover, the instrumentation system 100 can monitor responses of patients and research animals over hours, days, weeks, months, or years, for example.

In certain exemplary embodiments, the fluid 430 comprises a reagent or a material that facilitates an assay of the tissue 160. For example, the fluid 430 can comprise gold nanoparticles to facilitate a SERS analysis of the tissue 160 or an indicator or dye that fluoresces according to a condition, property, or constituent of the tissue 160. In certain embodiments, such a material can be delivered over the liquid core waveguide 150, with time provided to clear the catheter 155 in advance of spectral acquisition, for example.

In certain exemplary embodiments, the instrumentation system 100 acquires spectra during delivery of a pharmaceutical agent, with the agent contributing to the spectra. The spectra change as the agent exits the catheter 150. For example, the intensity of one or more Raman peaks associated with the pharmaceutical agent will typically diminish as the agent exits the liquid core waveguide 150. Accordingly, a medical practitioner, machine, or computer-based system can determine when the pharmaceutical agent has cleared the catheter 150 (or position within the catheter 150) based on spectral changes identified by the instrumentation system 100.

In certain exemplary embodiments, the fluid 430 comprises a high index liquid available from Cargille Laboratories, Inc. under the trade identifier CARGILLE Refractive Index Liquids, such as a liquid marketed under the identifier Series A with a refractive index in a range of 1.632 to 1.640, Series B with a refractive index in a range of 1.642 to 1.700, Series M with a refractive index in a range of 1.705 to 1.800, or Series H, EH, FH, or GH with a refractive index in a range of 1.81 to 2.31. Such liquids can be applied to industrial or non-biological applications, for example when the fluid 430 is toxic.

Figure 5B:
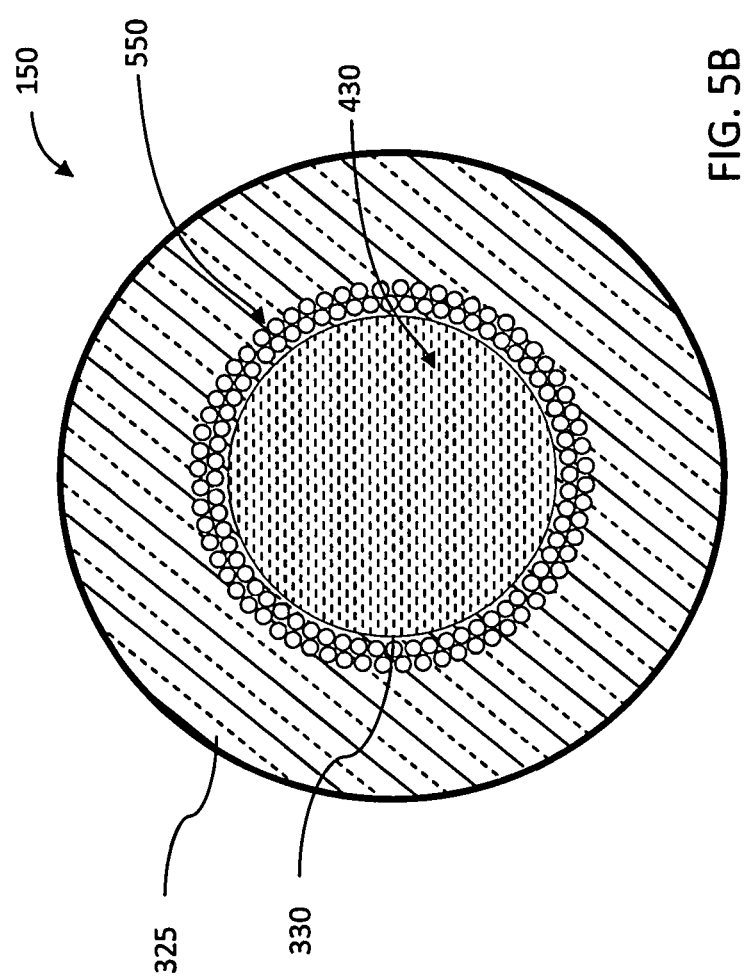
FIG. 5B is a cross sectional illustration of a liquid core waveguide in accordance with certain exemplary embodiments of the present invention.

Turning now to FIG. 5B, this figure is a cross sectional illustration of an exemplary liquid core waveguide 150 according to certain exemplary embodiments of the present invention. In the illustrated embodiment, the cladding 325 of the liquid core waveguide 150 comprises inclusions 550 that can be filled with gas, such as air.

In certain exemplary embodiments, the inclusions 550 are operative to reduce refractive index of the cladding 325 as encountered by the excitation light 170 and the return light 175. The inclusions 550 can extend lengthwise along the liquid core waveguide 150 adjacent the core 330. For example, the inclusions 550 can be hollow, tubular, or cylindrical cavities extending lengthwise along the liquid core waveguide 150. The inclusions 550 can be disposed within a range of about 3-15 microns of the physical edge of the core 330. In an exemplary embodiment, individual ones of the inclusions 550 have a diameter that is less than the wavelength(s) of the excitation light 170 and/or the analytically relevant return light 175. In an exemplary embodiment, each inclusion 550 has a cross sectional diameter that is sized to avoid substantial scattering losses of the excitation light 170 and the return light 175, such as due to Rayleigh and/or Mie scattering.

In certain exemplary embodiments, the inclusions 550 are oriented and/or sized to provide substantially level or ripple-free transmission of the return light 175 across the Raman fingerprint region or a spectral range of analytical utility to a tissue assay. In certain exemplary embodiments, the inclusions 550 are disposed to avoid establishing an optical resonance of the return light 175 that is a basis for the tissue assay. In certain exemplary embodiments, the inclusions 550 have a size distribution that avoids any detrimental photonic resonance. In certain exemplary embodiments, the inclusions 550 have different sizes towards avoiding such resonance. In certain exemplary embodiments, the inclusions 550 are sized with a standard deviation or with randomness. In certain exemplary embodiments, the inclusions are spaced apart from one another with randomness or in a non-repeating manner. In certain exemplary embodiments, the inclusions can be sized and or spaced in an unordered manner or as distinct from an ordered array or grid pattern.

In certain exemplary embodiments, the inclusions 550 are arranged in an ordered pattern. In certain exemplary embodiments, the inclusions 550 provide a crystal optical waveguide having a liquid core. In certain exemplary embodiments, the inclusions provide a photonic bandgap or band of reflectivity that is substantially flat or ripple free across the fingerprint region or another spectral range in which the tissue assay is conducted. In certain exemplary embodiments, any ripple is recorded in a computer-readable memory, and the instrumentation system corrects the ripple via execution of a software routine, which can be readily implemented by one of ordinary skill in the art having benefit of this disclosure. In certain exemplary embodiments, the liquid core waveguide 150 comprises a photonic crystal optical fiber with a central channel filled with the fluid 430. In certain exemplary embodiments, the liquid core waveguide 150 comprises a "microstructured" waveguide with a fluidic core. Microstructured and photonic crystal fibers appropriate for forming the cladding 325 of the liquid core waveguide 150 are commercially available, such as from Heraeus Tenevo LLC of Buford, Ga., USA.

Turning now to FIG. 6, this figure illustrates a flowchart of an exemplary process for conducting Raman spectroscopy according to certain embodiments of the present invention. Process 600, which is entitled Assay Tissue, will be discussed with exemplary reference to certain ones of the above described embodiments and figures. However, it will be appreciated that process 600 can operate with many other embodiments without limitation.

Certain steps in process 600, as well as in the other processes and methods disclosed or taught herein, may naturally need to precede others for the present invention to function as described. However, the present invention is not limited to the order of the steps described if such order or sequence does not adversely alter the functionality of the present invention to the extent of rendering the invention inoperable or nonsensical. That is, it is recognized that some steps may be performed before or after other steps or in parallel with other steps without departing from the scope and spirit of the present invention.

At step 605 of process 600, the liquid 430 flows through the fluid supply line 120 and fills the core 330 of the liquid core waveguide 150 through the fluid fitting 255.

At step 610 of process 600, the liquid 430 emits through the aperture 323 onto and/or into the tissue 160 that is the subject of assay. As discussed in further detail below, in certain exemplary embodiments, the aperture 323 can emit multiple liquids that collectively create a waveguide that forms a path through optically challenging media.

At step 620 of process 600, the laser 110 produces the excitation light 170, for example NIR light, that couples into the optical fiber 125. The excitation light 170 transmits over the optical fiber 125 to the filter system 140.

At step 625 of process 600, the filter system 140 substantially eliminates any unwanted or deleterious light or photonic noise that may have mixed with the excitation light 170 due to transmission over the optical fiber 125 or another source. In certain embodiments, step 625 can occur within the catheter 155. In certain embodiments, step 625 can occur outside the catheter 155.

At step 630 of process 600, the fluid 430, which can be viewed as impregnated with the excitation light 170, flows along the liquid core waveguide 150, through the aperture 323, and onto or into the tissue 160.

At step 635 of process 600, the illuminated tissue emits, produces, generates, or provides the return light 175, which can comprise Raman light in certain embodiments. The return light 175 passes through the aperture 323 and into the liquid core waveguide 150. The return light 175 transmits over the liquid core waveguide 150 towards the filtering system 140.

In certain exemplary embodiments, the return light 175 can return through an aperture that is separate from the aperture 320. For example, the return light 175 can be transmitted on a separate or dedicated liquid core waveguide having an associated aperture at its distal end. Thus, certain exemplary embodiments of the catheter 155 can comprise two or more liquid core waveguides, each providing a distinct light path.

At step 640 of process 600, the filtering system 140 couples the return light 175 to the optical fiber 135, which leads to the detector 115. The filtering system 140 substantially blocks the excitation light 170 from transmission over the optical fiber 135.

At step 645 of process 600, the return light 175 transmits to the detector 115, which typically converts the return light 175 into one or more electrical signals. In certain embodiments, the detector 115 creates an array of numbers, each represented as an electrical signal, describing intensity of the return light 175 as a function of wavelength.

At step 650 of process 600, the instrumentation system 100 analyzes the return light 175 to determine a condition or disease state of the tissue 160. In certain exemplary embodiments, return light processing and/or analysis is conducted in the optical domain. In certain exemplary embodiments, return light analysis is conducted in the electrical domain. In certain exemplary embodiments, return light processing and/or analysis is conducted in a combination of the electrical domain and the optical domain. A computer can determine the condition or disease state of the tissue 160 via executing one or more software routines based on spectral processing methods well known and readily implemented by those of ordinary skill in the art having benefit of this disclosure.

Following step 650, process 600 loops back to step 605 and iterates. Accordingly, tissue characterizing can continue substantially uninterrupted.

Technology for forming an optical path through optically challenging media will be described in further detail with reference to FIGS. 7, 8, 9, 10, and 11.

Turning now to FIG. 7, this figure illustrates, in two, orthogonal cross sectional views, an exemplary system for creating an optical channel through optical challenging media according to certain embodiments of the present invention. In the illustrated example, a catheter tip 700 forms the optical channel through blood 730 in a vascular lumen, such as an artery or vessel, of a patient. In an exemplary embodiment, the catheter 155 discussed above, and which FIG. 1 illustrates in exemplary form, can comprise the catheter tip 700. The catheter tip 700 is positioned a standoff distance from the wall 735 of the vascular lumen with blood 730 disposed in the standoff, for example by an interventional cardiologist during an interventional procedure.

The catheter tip 700 comprises a central channel 732, formed in a housing 725, through which the fluid 430 flows. The housing 725 is typically formed of or comprises optically transparent material, such as silica or silicate. As discussed above, the fluid 430 typically has a refractive index that is elevated above the refractive index of pure water. In an exemplary embodiment, the fluid 430 is or comprises water with dissolved salt or another material or combination of materials as discussed above.

Inclusions 550 circumferentially surround the central channel 732 to effectively reduce the refractive index of the portion of the housing 725 that forms a wall of the central channel 732. In an exemplary embodiment, the inclusions 550 can be smaller in at least one dimension than the wavelength of light flowing in the central channel 732 and can be filled with a gas such as air or carbon dioxide. Accordingly, light flowing along the central channel 732 encounters and interacts with the combination of inclusions 550 and the adjacent material of the housing 725 as having a refractive index that is substantially below that of the base material of the housing 725. The flowing light can be either or both of the excitation light 170 and the return light 175 illustrated in FIG. 1 and discussed above. As discussed above, the inclusions 550 and the associated material of the housing 725 form a cladding for guiding light in the central channel 732. In the illustrated embodiment, each inclusion 550 extends lengthwise. Alternatively, each inclusion 550 can be substantially ball-shaped or may be a bubble such that the inclusions 550 are dispersed along the exterior of the central channel 732, for example.

Peripheral channels 705 circumferentially surround the central channel 732 and the associated inclusions 550. The peripheral channels 705 extend lengthwise along the housing 725 and emit a fluid 710 having a refractive index that is lower than the refractive index of the fluid 430. For example, in certain exemplary embodiments, the fluid 710 can be water while the fluid 430 can be saline, saline solution, water saturated with sodium chloride, or an aqueous solution that comprises a salt. In certain exemplary embodiments, the fluid 710 and the fluid 430 both comprise water and salt, but the concentration of salt in the fluid 430 is higher than the concentration of salt in the fluid 710 such that the fluid 430 has an elevated refractive index. In certain exemplary embodiments, the fluid 710 and the fluid 430 comprise like ingredients, but the ingredient concentrations differ such that the fluid 430 has a higher refractive index than the fluid 710.

In certain exemplary embodiments, the fluid 710 comprises or is saline. In certain exemplary embodiments, the fluid 710 is normal saline. In certain exemplary embodiments, the fluid 710 is a solution of 0.91 percent weight/volume of sodium chloride (NaCl). In certain exemplary embodiments, the fluid 710 is about 300 mOsm/L. In certain exemplary embodiments, the fluid 710 is physiological saline or isotonic saline. In certain exemplary embodiments, the fluid 710 has a composition of about nine grams of NaCl per liter of water. In certain exemplary embodiments, the fluid 710 has a degree of osmolarity approximating blood or blood plasma or slightly suppressed below that of blood or blood plasma. In certain exemplary embodiments, the osmolarity of the fluid 710 approximates or approaches the osmolarity of NaCl in blood or blood plasma. In certain exemplary embodiments, the fluid 710 has a salinity that substantially matches or is reduced below the salinity of blood or blood plasma. In certain exemplary embodiments, the fluid 710 has an electrical conductivity approximating or suppressed below that of blood or blood plasma. In certain exemplary embodiments, the fluid 710 has a refractive index that is below the refractive index of blood or blood plasma. In certain exemplary embodiments, the fluid 710 is buffered and/or comprises a buffer. In certain exemplary embodiments, the fluid 710 has a composition that comprises salt, water, and one or more additives or agents having therapeutic, curative, or physiology benefit. In certain exemplary embodiments, the fluid 710 comprises, per liter, about 130 mEq of sodium ion, about 109 mEq of chloride ion, about 28 mEq of lactate, about 4 mEq of potassium ion, and about 3 mEq of calcium ion. In certain exemplary embodiments, the fluid 710 comprises sodium chloride, sodium lactate, calcium chloride, and/or potassium chloride. In certain exemplary embodiments, the fluid 710 is an alkalinizing solution. In certain exemplary embodiments, the fluid 710 is a saline solution. In certain exemplary embodiments, the fluid 710 substantially consists of inorganic ingredients or is substantially inorganic. In certain exemplary embodiments, the fluid 710 substantially consists of biocompatible ingredients or constituents. In certain exemplary embodiments, the fluid 710 has a refractive index below the refractive index of fused silica at the wavelength(s) of the excitation light 170 and/or the return light 175. In certain exemplary embodiments, the fluid 710 is substantially pure.

In certain exemplary embodiments, the fluid 710 can have a refractive index that is consistent with or substantially equal or equivalent to the refractive index provided by the combination of the wall of the housing 725 and the inclusions 550. Accordingly, light can smoothly pass between being guided by or reflected at the interface 755 between the fluid 430 and the fluid 710 and being guided by or reflected at the interface between the fluid 430 and the combination of the housing 725 and inclusions 550. Thus, light flowing in the fluid 430 can interact consistently with the fluid 710 and the combination of the housing 725 and the inclusions 550.

In certain exemplary embodiments, the fluid 710 and the fluid 430 flow from the catheter tip 700 at substantially the same speed and/or velocity. Thus, the emitted fluid 430 and the emitted fluid 710 can travel at substantially the same rate such that neither moves faster than the other. Alternatively, one can flow faster than the other. In certain exemplary embodiments the flow rate of the fluid 430 and the flow rate of the fluid 710 can be similar, such that the central channel 732 and the peripheral channels 705 emit substantially similar or equal volumes in a given amount of time. Alternatively, the flow rates can differ.

In certain exemplary embodiments, the emitted fluid 710 and the emitted fluid 430 can have a combined composition that approximates the salinity or refractive index of the blood 730. Thus, the mixed combination of the emitted fluid 710 and the emitted fluid 430 can have a concentration of one or more constituents or components approximating that of the blood 730 or its plasma. Accordingly, the volumes of the fluid 710 and the fluid 430 that flow out of the catheter tip 700 during a common period of time can, when mixed, have a concentration of one or more dissolved materials that is consistent or substantially equal to that of the blood 730 or of blood plasma. For example, the mixed combination can have a concentration of sodium chloride that is similar or equal to that of the blood 730 or its plasma. In certain exemplary embodiments, the mixed combination of the fluids 710 and 430 can: substantially be or comprise saline, normal saline, or a solution of 0.91 percent weight/volume of sodium chloride (NaCl); be about 300 mOsm/L; substantially be or comprise physiological saline or isotonic saline; have a composition of about nine grams of NaCl per liter of water; have a degree of osmolarity approximating blood or blood plasma or slightly elevated above blood or blood plasma; approximate or approach the osmolarity of NaCl in blood or blood plasma; have a salinity substantially matching the salinity of blood or blood plasma; have an electrical conductivity approximating that of blood or blood plasma; have a refractive index that approximates or substantially matches the refractive index of blood or blood plasma; be buffered and/or comprise a buffer; have a composition that comprises salt, water, and one or more additives or agents having therapeutic, curative, or physiology benefit; comprise, per liter, about 130 mEq of sodium ion, about 109 mEq of chloride ion, about 28 mEq of lactate, about 4 mEq of potassium ion, and about 3 mEq of calcium ion; comprise sodium chloride, sodium lactate, calcium chloride, and/or potassium chloride; be an alkalinizing solution or a saline solution; substantially consist of inorganic ingredients or be substantially inorganic; or substantially consist of biocompatible ingredients or constituents, to mention a few representative examples without limitation.

The emitted fluid 430 and the emitted fluid 710 form an interface 755 that guides light to and from the wall 735 of the vascular lumen. Accordingly, the interface 755 can provide a waveguide extending through the blood 730 between the catheter tip 700 and the wall 735 of the vascular lumen. In an exemplary embodiment, the interface 755 is internally reflective, for example creating a totally internally reflective interface. In certain exemplary embodiments, the interface 755 can provide a gradient refractive index for guiding light.

In certain exemplary embodiments, the emitted fluid 710 is circumferentially disposed about the emitted fluid 430. In certain exemplary embodiments, the emitted fluid 710 and the emitted fluid 430 are disposed in a coaxial or substantially coaxial arrangement or configuration. In certain exemplary embodiments, the emitted fluid 710 and the emitted fluid 430 form a column, jet, or plume of fluid, have a substantially cylindrical or elongated form, and/or exhibit symmetry about a common longitudinal axis.

Figure 7B:
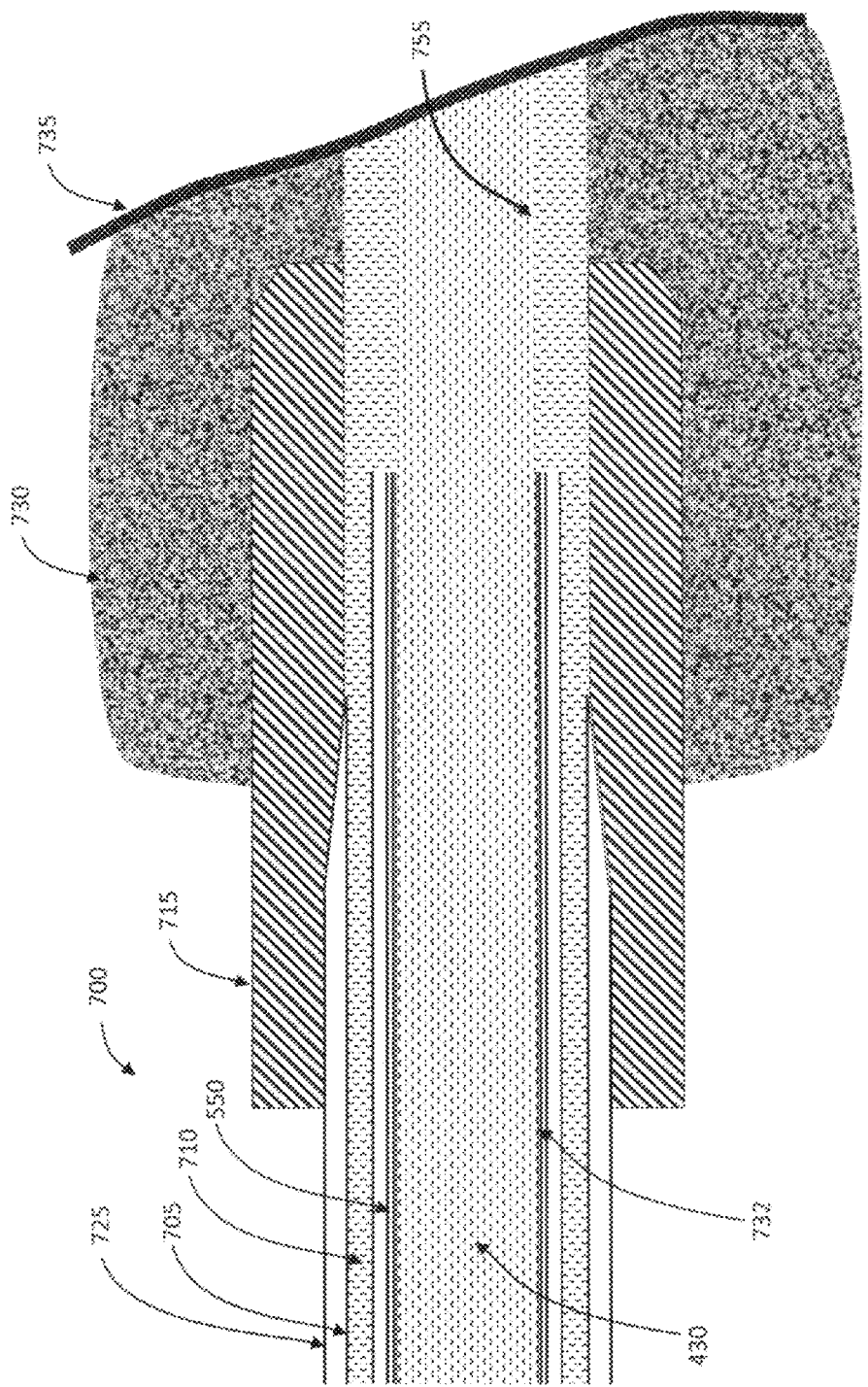

As illustrated in FIG. 7B, in certain exemplary embodiments, the catheter tip 700 can comprise an extension 715 that helps launch the fluids 710 and 430 to provide a waveguiding geometry or configuration. (FIG. 7B illustrates the extension 715 with exaggerated wall thickness to the benefit of reader visualization.) For example, the extension 715 can help avoid turbulence and/or premature mixing of the fluids 710 and 430 and/or help maintain the interface 755 in a format that guides light. Further, the extension 715 can shield the flowing fluids 710 and 430 from disturbance or disruption by flow of the blood 730. In certain exemplary embodiments, the extension 715 can be formed of substantially rigid material, such as glass, quartz, ceramic, or stainless steel. In certain exemplary embodiments, the extension 715 can be pliable, for example formed of an elastomer or an elastomeric material. In certain exemplary embodiments, the extension 715 can have a wall thickness that is less than about 0.001 or 0.0005 inches or about 5, 10, or 20 microns or in a range thereof, for example. In certain exemplary embodiments, the extension 715 can be or comprise a thin walled fluoropolymer tube that may be rolled up or otherwise stowed prior to deployment. Accordingly, the extension 715 can deploy and extend in response to the fluids 710 and 430 flowing form the catheter tip 700, for example.

In an exemplary embodiment that is a variation of the illustration of FIG. 7, a fluid having a low index of refraction may flow out of the inclusions 550 rather than the peripheral channels 705 (or in addition to the peripheral channels 705). If not used for fluid delivery, the peripheral channels 705 can be eliminated. In such embodiments, light flowing within the catheter tip 700 can interact with a combination of the housing and the fluid in the inclusions. Accordingly, the inclusions 550 can delivery the fluid 710, various embodiments and compositions of which are disclosed herein.

Figure 8:
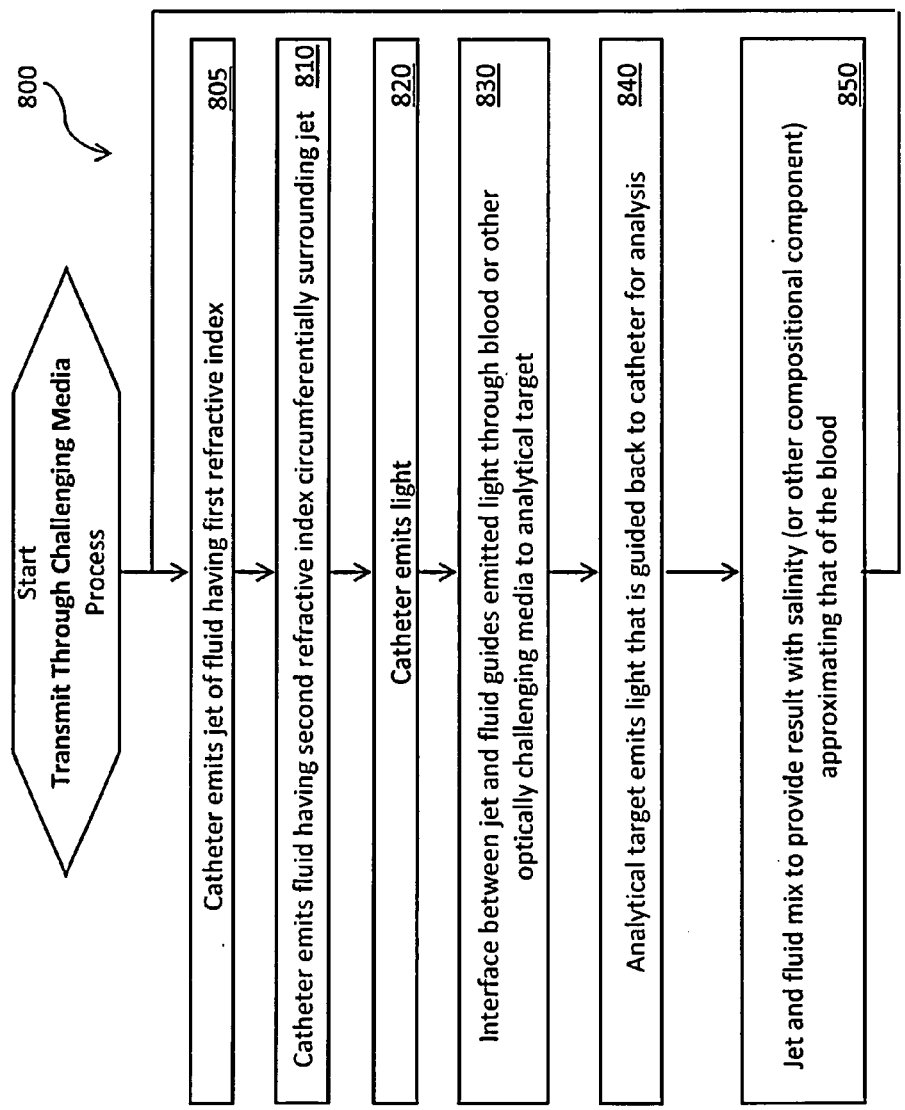
FIG. 8 is a flow chart of a process for creating an optical channel through optical challenging media and conducting a material analysis via transmitting light over the channel in accordance with certain exemplary embodiments of the present invention.

Turning now to FIG. 8, this figure illustrates a flow chart of an exemplary process 800 for creating an optical channel through optical challenging media and conducting a material analysis via transmitting light over the channel according to certain embodiments of the present invention. The process 800, which is entitled "Transmit Through Challenging Media," will be discussed with exemplary reference to FIG. 7, as discussed above.

At step 805 of process 800, the catheter tip 700 emits a jet, column, elongated flow, cylinder, or flow having a generally circular or oval cross section, a cylinder-like or cylindrical flow, or other suitable geometric configuration of fluid the fluid 430. The flow pattern of the fluid 430 extends through the blood 730 towards (and in certain embodiments to) the wall 735 of the vascular lumen. The blood 730 is an example of an optically challenging media. Other examples may include colloids, turbid fluids, suspensions, absorbers, agitated or flowing mixtures, combinations of solids and liquids, combinations of liquids and gas, inks, mud, silt, milk, smoke, airborne debris, or other fluid that may scatter and/or absorb light detrimentally or excessively.

At step 810, the catheter tip 700 emits the fluid 710. In an exemplary embodiment, steps 805 and 810 can execute in parallel or simultaneously. The fluid 710 typically circumferentially surrounds the fluid 430. For example, the fluid 710 can have a geometric form of a hollow cylinder or tube with the fluid 430 disposed therein. The fluid 710 can form a cladding for the fluid 430. In certain exemplary embodiments, the fluid 710 and the fluid 430 can flow in a substantially coaxial arrangement. In certain exemplary embodiments, the fluid 430 and the fluid 710 can be disposed around or have a substantially common or collinear axis or line of symmetry.

At step 820, the catheter tip 700 emits light into the fluid 430, which can be the excitation light 170 illustrated in FIG. 1 and discussed above. The light flows within the fluid 710. As step 830, an interface 755 formed between the fluid 430 and the fluid 710 guides the emitted light, typically by internal reflection. The interface 755 can maintain the light on or in an optical channel that transmits the light to the analytical target, in this example the wall 735 of the vascular lumen. Accordingly, the interface 755 helps keep the light concentrated and on course through the blood 730 for incidence on the wall 735. The resulting channel can substantially isolate the light from detrimental interaction with the blood 730 in advance reaching the wall 735.

At step 840, the analytical target, in this example the wall 735 of a vascular lumen, emits or produces light in response to the illumination. In an exemplary embodiment, light emitting from the wall 735 can be the return light 175 illustrated in FIG. 1 and discussed above. The optical channel through the blood 730 formed by the fluid 430 and the fluid 710 guides the light that the wall 735 emits back to the catheter tip 700. The catheter tip 700 carries that light back to the catheter 155 for delivery to the detector 115 as illustrated in FIG. 1 and discussed above. The detector 115 can process the light and determine vulnerability to rupture or another parameter of the wall 735 of the vascular lumen having clinical or research significance.

At step 850, the fluid 430 and the fluid 710 mix. For example, the fluid 430 and the fluid 710 can mix in connection with flowing against the wall 735 of the vascular lumen. The combined fluids 430 and 710 can provide a mixture or solution that has a salinity, or some other biologically relevant parameter or condition, that approximates or equals that of the blood 730. The combination of the fluids 430 and 710 can be biologically compatible and can be introduced into a vasculature (or other system) of a patient with minimal negative impact. Following step 850, process 800 loops back to step 805 and iterates or continues.

Turning now to FIG. 9, this figure illustrates an exemplary system for analyzing a material via delivering and collecting light according to certain embodiments of the present invention. More specifically, FIG. 9A and FIG. 9B respectively illustrate a side view and an end-on view of a fiber optic probe 900. The fiber optic probe 900 can be disposed or attached at the tip of a catheter, such as the catheter 155 illustrated in FIG. 1 and discussed above, integrated into a surgical needle, such as the needle 165 illustrated in FIG. 3 and discussed above, or otherwise employed for medical usages, research, pharmaceutical development or production, industrial, chemical process control, supervisory control and data acquisition ("SCADA"), or manufacturing application, for example.

The fiber optic probe 900 comprises a delivery fiber 920 and a return fiber 930 that extend in a housing 910, which can be either flexible or rigid, to a distal end. In various exemplary embodiments, the housing 910 can be or comprise an elastomer, polymer, thermoplastic, fluoropolymer, metal, ceramic, or other appropriate material, for example formed into a tube or tubular format.

In the illustrated embodiment, the return fiber 930 is larger in diameter than the delivery fiber 920. In other embodiments, the return fiber 930 and the delivery fiber 920 can have like diameters, and either or both can comprise a bundle of optical fibers. The delivery fiber 920 transmits the excitation light 170 to a fiber optic segment 915 butted up to the delivery fiber 920. A band pass filter 925 disposed between the delivery fiber 920 and the fiber optic segment 915 suppresses, attenuates, rejects, or blocks interference propagating in the fiber optic probe 900 along with the excitation light 925, which can be laser light and/or substantially monochromatic. In certain embodiments, an edge filter can be substituted for the band pass filter 925. The band pass filter 925 (as well as other filters that the fiber optic probe 900 comprises) can comprise a multi-cavity thin-film interference filter comprising layers of alternating refractive index optical materials, such as tantalum pentaoxide and silicon dioxide for example.

The fiber optic segment 915 comprises an angled end face 917 that is coated with a notch filter or an edge filter. So coated, the angled end face 917 transmits interference to the light trap 905 but reflects the excitation light 925. The light trap 905, which can comprise epoxy loaded with carbon black, absorbs the interference.

The angled end face 917 reflects the excitation light 170 to the angled end face 940 of the fiber optic segment 935, which is butted up to the return fiber 930. The angled end face 940 reflects the excitation light 170 to a target for analysis, such as the wall 735 of the vascular lumen illustrated in FIG. 7B and discussed above or the tissue 160 illustrated in FIG. 1 and discussed above. The angled end face 940 can be coated with a thin-film interference filter that transmits the return light 175 and reflects the excitation light 170, for example. In certain exemplary embodiments, such a filter can be a notch filter or an edge filter, for example. An edge filter can be a filter that transmits light having a wavelength above a threshold and reflects light having a wavelength below a threshold or that transmits light having a wavelength below a threshold and reflects light having a wavelength above a threshold.

In response to interaction with the excitation light 170, the target emits the return light 175, for example via Raman scattering. The return light 175 passes through the angled end face 940, for example as a result of being wavelength shifted from the excitation light 170 and thus in a transmission band or region of a filter coating applied to the angled end face 940.

The fiber optic segment 935 transmits the return light 175 to the return fiber 930, through a filter 945 disposed between the fiber optic segment 935 and the return fiber 930. The filter 945 suppresses, attenuates, rejects, or blocks the excitation light 170 from transmitting on the return fiber 930, thereby avoiding the excitation light 170 from generating interference on the return fiber 930. In an exemplary embodiment, the filter 945 can be an edge filter or a notch filter. The return fiber 930 typically transmits the return light 175 to a spectroscopic system that spectrally analyzes the return light 175 to characterize the target, for example determining composition and/ or rupture vulnerability of plaque on the wall 735 of the vascular lumen.

Additional information about making and using exemplary fiber optic probes, including information relevant to exemplary embodiments and variations of the fiber optic probe 900 illustrated in FIG. 9, is available in U.S. Pat. No. 6,366,726, entitled "Fiber Optic Probes for Indwelling Investigations," and issued on Apr. 2, 2002 in the name of Wach et al.

The exemplary fiber optic probe 900 illustrated in FIG. 9 comprises a channel 960 for emitting a liquid or gas that creates an optical path through challenging media such as the blood 730 illustrated in FIG. 7B and discussed above. In the fiber optic probe 900, the channel 960 is formed between the housing 910 and the optical elements disposed therein. In certain exemplary embodiments, the channel 960 can comprise interstitial spacing between optical fibers and/or other elements of the fiber optic probe 900. The channel 960 can comprise a cross sectional gap between elements that extends longitudinally. In certain exemplary embodiments, the fiber optic probe 900 can comprise a lengthwise running tube that provides the channel 960.

In certain exemplary embodiments, the fiber optic probe 900 creates an optical path through optically challenging media via the channel 960 emitting carbon dioxide or another appropriate gas. The carbon dioxide can be emitted in pulses or intermittently and/or as a jet or column, for example. In an exemplary embodiment, the fiber optic probe 900 can be positioned near the wall 735 of the vascular lumen, with blood 730 disposed between the distal end of the fiber optic probe 900 and the wall 735. The emitted carbon dioxide can displace most or substantially all of such intervening blood 730. Accordingly, the fiber optic probe 900 can analyze the wall 735 of the vascular lumen free from the level of interference from blood 730 that would otherwise exist. Relative to nitrogen and many other gases, carbon dioxide has high solubility in the blood 730 and thus avoids issues that introduction of low-solubility gases may cause.

In certain exemplary embodiments, the channel 960 can emit a liquid such as saline solution or blood plasma. In certain exemplary embodiments, the channel 960 can emit any appropriate one or ones of the materials described above as examples of the fluid 430 or the fluid 710. In certain exemplary embodiments, the channel 960 can emit the fluid 430 or the fluid 710.

Turning now to FIG. 10, this figure illustrates an exemplary system for analyzing a material via delivering and collecting light according to certain embodiments of the present invention. More specifically, FIG. 10 illustrates a fiber optic probe 1000 that comprises a balloon 1005A, 1005B attached to an embodiment of the fiber optic probe 900 illustrated in FIG. 9 and discussed above. FIG. 10A illustrates the fiber optic probe 1000 with the balloon 1005A in a deflated or relaxed state, while FIG. 10B illustrates the fiber optic probe 1000 with the balloon 1005B inflated. The fiber optic probe 1000 further comprises an optic 1010 for managing delivery of excitation light 170 and reception of return light 175.

As discussed above with reference to FIG. 9, the fiber optic probe 1000 can be positioned near the wall 735 of a vascular lumen or another site or material of interest. For example, the fiber optic probe 1000 can be pointed generally towards an investigative site. Inflating the balloon 1005A, 1005B displaces the blood 730 or other optically challenging media disposed between the fiber optic probe 1000 and an investigative site, such as the wall 735. Accordingly and as illustrated in FIG. 10B, the fiber optic probe 1000 forms an optical channel through the optical challenging media to facilitate coupling excitation light 170 to and return light 175 from the site. In an exemplary embodiment, the blood 730 can continue to flow while the balloon 1005B is inflated. Thus, the fiber optic probe 1000 can characterize cardiovascular structures at or in the wall 735 without blood flow occlusion. (Nevertheless, in some applications or circumstances, occlusion may be appropriate.)

As illustrated, the balloon 1005A, 1005B projects or extends lengthwise, generally along the longitudinal axis of the fiber optic probe 1050. Alternatively, a balloon can extend laterally from a side of the fiber optic probe 1050, with light following the path of balloon extension—in which case the fiber optic probe 1050 can be outfitted with one or more mirrors or otherwise configured for side viewing.

In certain exemplary embodiments, in an extended state of use the balloon 1005B can have a diameter that is in a range of about 1 to 10 times the diameter of the fiber optic probe 1000. Various other inflated balloon diameters can be about 1.5, 2, 3, 5, 8, 10, 12, 15, 18, 20, or 25 times the diameter of the fiber optic probe 1000 or the diameter of an optical fiber or in a range between any two of the values in this sentence. In certain exemplary embodiments, the inflated balloon 1005B has a diameter of approximately 200, 300, 500, 750, 1,000, 1,500, 2,000, 2,500, 3,000, 4,000, or 5,000 microns or in a range between any two of the numbers in this sentence. In certain exemplary embodiments, the inflated balloon 1005B has a diameter of about 200, 300, 500, 750, 1,000, 1,500, 2,000, 2,500, 3,000, 4,000, or 5,000 microns or in a range between any two of the numbers in this sentence. In certain exemplary embodiments, the inflated balloon 1005B has a length that is about 5, 10, 15, 20, 25, 30, 40, 50, 75, or 100 times the diameter of the fiber optic probe 1000, or in a range of any two of the numbers in this sentence.

The balloon 1005A, 1005B can be attached to the body of the fiber optic probe 900 with epoxy, crimping, squeezing, pinching, bonding, or other appropriate fastening and/or another appropriate sealing technique or means known in the art. The balloon 1005A, 1005B can be formed of an appropriate elastomeric material as known in the art. Spectral contribution of the balloon 1005B to the return light 175 can be subtracted or referenced out. That is, any artifact associated with transmitting light through the wall of the inflated balloon 1005B can be removed by a computer processing a digital representation of the return light 175 (or a spectra thereof) using well known processing methods.

Emitting optically compatible or transparent material from the channel 960 (see FIG. 9B) inflates the balloon 1005B, transitioning from the state of FIG. 10A to the state of FIG. 10B. For example, the channel 960 can emit a gas, such as carbon dioxide or a liquid, such as water or saline solution, as discussed above with reference to FIG. 9 (or other appropriate material as discussed above).

Figure 11:
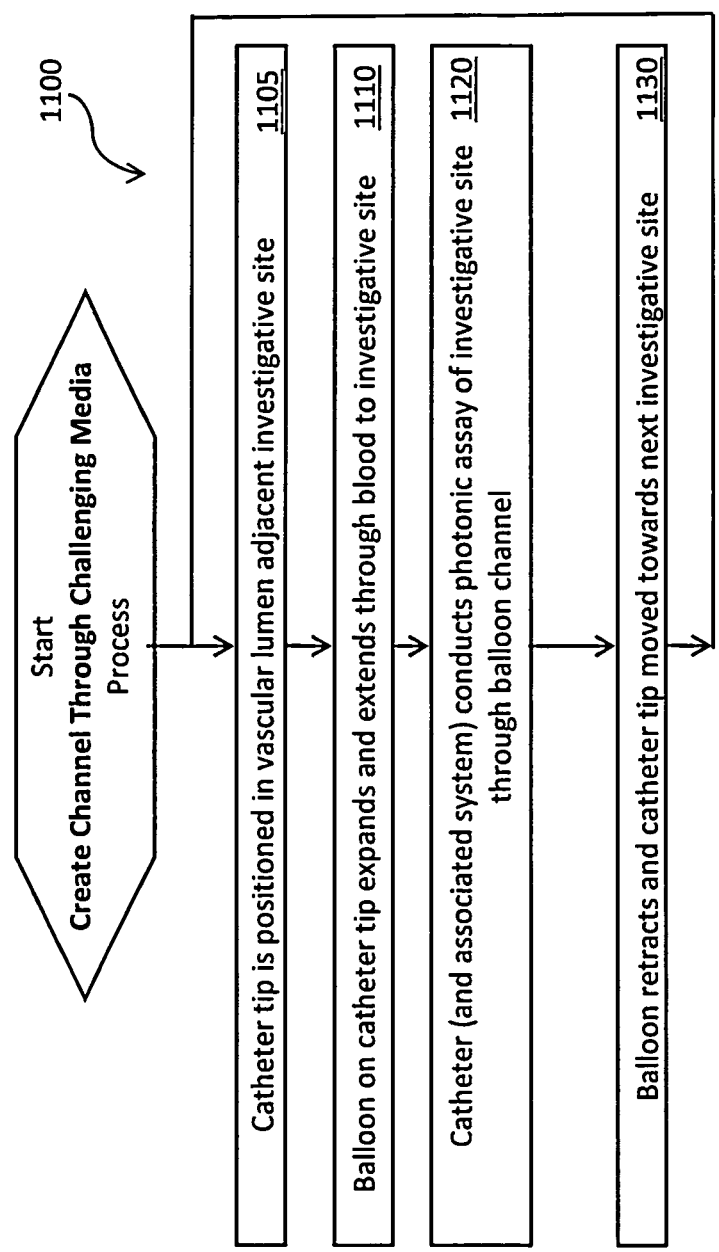
FIG. 11 is a flow chart of a process for creating an optical channel through optical challenging media in accordance with certain exemplary embodiments of the present invention.

Turning now to FIG. 11, this figure illustrates a flow chart of an exemplary process 1100 for creating an optical channel through optical challenging media according to certain embodiments of the present invention. Process 1100, which is entitled "Create Channel Through Challenging Media," will be discussed with exemplary reference to FIGS. 9 and 10, as discussed above.

At step 1105 of process 1100, a medical practitioner such as an interventional cardiologist or an assistant orients a catheter tip adjacent a lesion or plaque of interest within a vascular lumen. In this example, the catheter tip comprises the fiber optic probe 1000. The medical practitioner may point the fiber optic probe 1000 directly at the investigative site or position the fiber optic probe 1000 alongside the site, for example.

At step 1110, the channel 960 of the fiber optic probe 1000 emits an optically compatible fluid into the balloon 1005A. The optically compatible fluid can be a gas such as carbon dioxide or a transparent liquid such as saline solution. In response to the fluid, the balloon 1005B expands and extends through the blood 730 and to the investigative site at the wall 735 of the vascular lumen as illustrated in FIG. 10B. FIG. 10B illustrates the balloon 1005B projecting substantially along the longitudinal axis of the fiber optic probe 1000. Alternatively, the balloon 1005B may extend and project laterally from the fiber optic probe 1000. For example, the balloon 1005B can jut out from one side of the fiber optic probe 1000 and/or extend substantially perpendicular to the fiber optic probe 1000. Accordingly, the axis or line of the balloon's extension can be substantially collinear with the fiber optic probe 1000, can divert or diverge from the longitudinal axis of the fiber optic probe 1000, or can be substantially perpendicular to the longitudinal axis of the fiber optic probe 1000, for example. The balloon 1005B typically contacts the wall 735 of the vascular lumen at a specific circumferential location of the lumen, such that other circumferential locations remain unobstructed and blood 730 can flow through the lumen free from occlusion.

At step 1120, the fiber optic probe 1000 (and associated catheter 155 and instrumentation system 100 as illustrated in FIG. 1) conducts a photonic assay or light-based analysis of the selected site on the wall 735 of the vascular lumen. The assay can evaluate chemical composition, morphology, extent of inflammation, oxidative stress, tissue structure, physical attributes of tissue, one or more images, or some other appropriate parameter of interest. As discussed above, the fiber optic probe 1000 can use the internal volume of the expanded balloon 1005B to provide an optical channel or path extending through the blood 730 to the wall 735 of the vascular lumen.

At step 1130, the fiber optic probe 1000 deflates the balloon 1005B via the channel 960 transmitting fluid out the balloon 1005B. With the balloon 1005A deflated as illustrated in FIG. 10A, the medical practitioner (or biomedical researcher) can navigate the fiber optic probe 1000 within the vasculature of a patient or a laboratory animal. Following step 1130, process 1100 loops back to step 1105, and the medical practitioner may elect to position the fiber optic probe 1000 for analyzing other regions of the vascular lumen or a different vascular lumen. Process 1100 can continue iterating until the practitioner is satisfied that the medical procedure (or research session) is complete.

Exemplary embodiments of the present invention can be described in many ways. For example, certain exemplary embodiments of the present invention can comprise a method for analyzing a material. The method can comprise the steps of: receiving first light at a first end of a first optical fiber and transmitting the first light over the first optical fiber; coupling the first light from a second end of the first optical fiber to a first end of a waveguide and transmitting the first light over the waveguide; emitting the first light from a second end of the waveguide to an analyte, wherein the analyte emits second light in response to interaction with the first light; receiving the second light at the second end of the waveguide; transmitting the second light from the second end of the waveguide to the first end of the waveguide; and coupling the second light from the first end of the waveguide to a second optical fiber for transmission to a detector, wherein the waveguide comprises a liquid core circumferentially surrounded by a solid cladding. In certain embodiments of the method, the analyte and second end of the waveguide are disposed inside a mammalian organism. In certain embodiments of the method, a cardiac catheter comprises the waveguide. In certain embodiments of the method, the liquid core comprises saline, and wherein the solid cladding is substantially inorganic. In certain embodiments of the method, the step of emitting the first light from the second end of the waveguide comprises flowing liquid through the liquid core and onto the analyte. In certain embodiments of the method, the solid cladding comprises silica and a plurality of gas-filled inclusions that are operative to reduce refractive index of the cladding relative to the liquid waveguide to provide a totally internally reflective interface between the cladding and the liquid waveguide.

Certain exemplary embodiments of the present invention can comprise a method for material analysis. The method can comprise the steps of: producing Raman light in response to an optical waveguide emitting laser light into a biological material; and analyzing the biological material in response to the optical waveguide receiving the Raman light and transmitting the Raman light for receipt by a detector for spectral analysis, wherein the optical waveguide comprises: a flexible silica tube providing a first refractive index; and a substantially inorganic aqueous solution disposed in the flexible silica tube and extending lengthwise and providing a second refractive index that is substantially higher than the first refractive index. In certain embodiments of the method, the first refractive index and the second refractive index are selected to provide the optical waveguide with a numerical aperture substantially matching a spectrometer or an optical fiber that is coupled to the optical waveguide. In certain embodiments of the method, the optical waveguide is a single mode optical waveguide, the substantially inorganic aqueous solution disposed in the flexible silica tube comprises a waveguide core, and the flexible silica tube comprises a waveguide cladding. In certain embodiments of the method, at least part of the optical waveguide is disposed inside a patient who comprises the biological material. In certain embodiments of the method, a catheter sized for insertion in a vascular lumen of a human comprises the optical waveguide. In certain embodiments of the method, a wetted interface between the substantially inorganic aqueous solution and the flexible silica tube is totally internally reflective and is operable to guide the laser light towards the biological material and the Raman light towards the detector. In certain embodiments of the method, the laser light has a wavelength, the flexible silica tube comprises an annular section that circumferentially surrounds the substantially inorganic aqueous solution within a distance of about ten times the wavelength from the substantially inorganic aqueous solution, the annular section comprises a plurality of cavities that are disposed circumferentially about the substantially inorganic aqueous solution, that are filled with one or more gases, and that are operative to impart the annular section with the first refractive index, the first refractive index is substantially lower than a refractive index of pure silica, and the annular section is operative to provide substantially uniform internal reflection across a fingerprint spectral region of the Raman light.

Certain exemplary embodiments of the present invention can comprise a method for analyzing a biological material. The method can comprise the steps of: providing a waveguide that comprises: a core comprising saline solution; and a cladding comprising silica and one or more gases, wherein an interface between the core and the cladding is operative to provide total internal reflection across a range of wavelengths; inserting at least a portion of the waveguide into the biological material; causing the biological material to emit light in response to the waveguide propagating laser light in a first direction and emitting the laser light onto the biological material; receiving the emitted light from the biological material and propagating the emitted light over the waveguide in a second direction opposite the first direction; and analyzing the biological material in response to processing the received emitted light, wherein the laser light and the received emitted light are in the range of wavelengths. In certain embodiments of the method, the range of wavelengths comprises a fingerprint region of a Raman spectrum of the biological material produced by the laser light. In certain embodiments of the method, the inserting step comprises inserting a cardiac catheter into a human being, and the waveguide comprises a single mode waveguide. In certain embodiments of the method, the biological material comprises a portion of a vascular lumen that is disposed inside a living organism, and the waveguide propagating laser light comprises the laser light propagating through a flowing stream of the saline solution. In certain embodiments of the method, the biological material comprises a tumor, aneurismal tissue, or vascular deformity inside a patient. In certain embodiments of the method, processing the received emitted light comprises segregating the laser light from the received emitted light with one or more optical filters and spectrally analyzing at least a portion of the received emitted light. In certain embodiments of the method, the range of wavelengths comprises at least twenty nanometers.

Certain exemplary embodiments of the present invention can comprise a method for coupling light across an optically challenging medium. The method can comprise the steps of: disposing an end of an optical fiber in the medium; forming an optical path through the medium in response to emitting a first fluid and a second fluid into the medium, wherein the second fluid circumferentially surrounds the first fluid in a substantially coaxial arrangement, wherein the second fluid has a lower refractive index than the first fluid, and wherein an interface between the first fluid and the second fluid is substantially reflective; coupling light between the optical fiber and the optical path; and guiding light along the optical path via the substantially reflective interface, the guided light coupling across the medium. In certain embodiments of the method, coupling light between the optical fiber and the optical path comprises the optical fiber emitting the light. In certain embodiments of the method, coupling light between the optical fiber and the optical path comprises the optical fiber receiving the light. In certain embodiments of the method, coupling light between the optical fiber and the optical path comprises the optical fiber emitting laser light at one end of the optical path for transmission to an analyte and receiving light that the analyte has emitted in response to illumination by the laser light. In certain embodiments of the method, the light comprises Raman light emitted from an analyte disposed at an end of the optical path opposite the optical fiber. In certain embodiments of the method, the medium comprises blood and a catheter comprises the optical fiber.

Certain exemplary embodiments of the present invention can comprise a method. The method can comprise the steps of: disposing an end of a catheter in a vascular lumen that is substantially filled with blood, the end comprising an optical fiber; orienting the end with respect to a region of a wall of the vascular lumen; in response to inflating a balloon attached to the catheter, providing an optical path that extends through the blood from the end to the region; and assaying the region in response to coupling light between the optical fiber and the region over the provided optical path, wherein blood flows through the vascular lumen while the balloon is inflated. In certain embodiments of the method, inflating the balloon comprises the balloon projecting laterally from the catheter. In certain embodiments of the method, inflating the balloon comprises the balloon projecting from the end substantially along a longitudinal axis of the catheter. In certain embodiments of the method, the assaying step comprises: illuminating the region with laser light; receiving Raman light emitted from the region; and evaluating composition of the region in response to spectrally analyzing the received Raman light. In certain embodiments of the method, the region is an atherosclerotic lesion. In certain embodiments of the method, inflating the balloon comprises disposing carbon dioxide in the balloon. In certain embodiments of the method, a distal end of the optical fiber is displaced at least about three millimeters from the region while coupling light between the optical fiber and the region over the optical path, the region comprises an atherosclerotic plaque, and the method comprises determining whether the plaque is vulnerable to rupture. In certain embodiments of the method, assaying the region comprises determining composition of the region via spectrally analyzing the light and compensating for spectral contribution of the balloon.

Certain exemplary embodiments of the present invention can comprise a method for analyzing a vascular lumen of a live animal. The method can comprise the steps of: disposing in the vascular lumen an end of a catheter that comprises an end face of an optical fiber; orienting the end with respect to a plaque of the vascular lumen, wherein blood is disposed between the end face and the plaque; displacing the blood and clearing an optical path between the end and the plaque in response to emitting a gas from the end; and transmitting light across the cleared optical path while blood flow continues substantially uninterrupted in the vascular lumen. In certain embodiments of the method, emitting the gas from the end comprises the emitted gas contacting the blood. In certain embodiments of the method, the gas comprises carbon dioxide. In certain embodiments of the method, the gas is absorbed by blood flowing in the vascular lumen. In certain embodiments of the method, the light comprises laser light that causes the plaque to produce Raman light for analysis. In certain embodiments of the method, the gas is more dissolvable in the blood than nitrogen.

Technology useful for creating optical paths through challenging media and for light-based characterization of a wide range of materials has been described, including but not limited to Raman analyses of in vivo tissues. From the description, it will be appreciated that an embodiment of the present invention overcomes limitations of the prior art. Those skilled in the art will appreciate that the present invention is not limited to any specifically discussed application or implementation and that the embodiments described herein are illustrative and not restrictive. Furthermore, the particular features, structures or characteristics that are disclosed may be combined in any suitable manner in one or more embodiments based on this disclosure and ordinary skill. Those of ordinary skill having benefit of this disclosure can make, use, and practice a wide range of embodiments via combining the disclosed features and elements in many permutations without undue experimentation. This disclosure not only includes the illustrated and described embodiments, but also provides a rich and detailed roadmap for creating many additional embodiments using the various disclosed technologies, elements, features, and their equivalents. From the description of the exemplary embodiments, equivalents of the elements shown herein will suggest themselves to those skilled in the art, and ways of constructing other embodiments of the present invention will appear to practitioners of the art. Therefore, the scope of the present invention is to be limited only by the accompanying claims.

What is claimed is:

1. A method for coupling light across an optically challenging medium, comprising:
    emitting, from a fluid delivery device having a first channel, a second channel circumferentially surrounding the first channel, and an extension circumferentially surrounding the second channel and projecting in a fluid delivery direction beyond respective distal ends of the first and second channels, a first fluid from the first channel and emitting a second fluid from the second channel, the first and second fluids, upon being emitted, displacing the medium so as to form an optical path through the medium, wherein, in the medium, the second fluid circumferentially surrounds the first fluid in a substantially coaxial arrangement, wherein the second fluid has a lower refractive index than the first fluid, and wherein an interface between the first fluid and the second fluid is substantially reflective;
    optically coupling a first end of an optical fiber to a first end of the optical path; and
    guiding light from the first end of the optical fiber along the optical path through the medium via the substantially reflective interface to a target located proximate to a second end of the optical path, the second end of the optical path located opposite to the first end of the optical path,
    wherein the second fluid is not identical to the medium being displaced.

2. The method of claim 1, wherein the medium comprises blood, and wherein a catheter comprises the optical fiber.

3. The method of claim 1, further comprising guiding light from the target along the optical path through the medium via the substantially reflective interface.

4. The method of claim 1, wherein the first channel is formed by a central channel and the second channel is formed by a plurality of peripheral channels circumferentially surrounding the central channel.

* * * * *